US005386025A

United States Patent [19]

Jay et al.

[11] Patent Number: 5,386,025

[45] Date of Patent: Jan. 31, 1995

[54] CALCIUM CHANNEL COMPOSITIONS AND METHODS

[75] Inventors: Scott D. Jay, Iowa City, Iowa; Steven B. Ellis; Michael M. Harpold, both of San Diego, Calif.; Kevin P. Campbell, Iowa City, Iowa

[73] Assignee: The Salk Institute Biotechnology/Industrial Associates, San Diego, Calif.

[21] Appl. No.: 482,384

[22] Filed: Feb. 20, 1990

[51] Int. Cl.[6] .................... C07H 21/02; C07H 21/04; C12Q 1/68; C12N 5/10

[52] U.S. Cl. .................................. 536/23.5; 435/6; 435/240.2

[58] Field of Search .................... 536/27, 23.5; 435/6, 435/240.2; 935/77, 78

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/387 |
| 4,954,436 | 9/1990 | Froehner et al. | 435/7 |
| 5,024,939 | 6/1991 | Gorman | 435/69.1 |

FOREIGN PATENT DOCUMENTS

| | | |
|---|---|---|
| 8907608 | 8/1989 | WIPO . |
| 8909834 | 10/1989 | WIPO . |
| 9304083 | 3/1993 | WIPO . |

OTHER PUBLICATIONS

Ellis et al, Science, vol. 241, Sep. 23, 1988, pp. 1661–1664.

Jay et al, Science, vol. 248, Apr. 17, 1990, pp. 490–492.

Spedding et al., "'Calcium Antgonists': A Class of Drugs with a Bright Future. Part II. Determination of Basic Pharmacological Properties", *Life Sciences* 35:575–587 (1984).

Kim, et al., "IgG from patients with Lambert-Eaton syndrome blocks voltage-dependent calcium channels," *Science*, 239: 450–408 (1988).

Claudio, et al., "Genetic reconstitution of functional acetylcholine receptor channels in mouse fibroblasts," *Science*, 238: 1688–1694 (1987).

Tanabe, et al., "Primary structure of the receptor for calcium channel blockers from skeletal muscle," *Nature*, 328: 313–318 (1987).

Nakayama, et al., "Purification of a putative $Ca^{2+}$ channel protein from rabbit skeletal muscle," *J.Biol.Chem.*, 262: 6572–6576 (1987).

Vaghy et al., "Identification of a novel 1,4–dihydropyridine— and phenylalkylamine— binding polypeptide in calcium channel preparations," *J. Biol. Chem.*, 262(29): 14337–14342 (1987).

Leung, et al., "Structural characterization of the 1,4–dihydrophyridine receptor of the voltage-dependent $Ca^{2+}$ channel from rabbit skeletal muscle," *J. Biol. Chem., 262(17): 7943–7946 (1987).*

Sharp, et al., "Identification and characterization of the dihydropyridine-binding subunit of the skeletal muscle dihydropyridine receptor," *J.Biol.Chem.*, 62(25): 12309–12315 (1987).

Takahashi, et al., "Subunit structure of dihydropyridine-sensitive calcium channels from skeletal muscle," *Proc.Natl.Acad.Sci. (USA), 84: 5478–5482 (1987).*

Morton et al., "Monoclonal antibody identifies a 200–kDA subunit of the dihydropyridine-sensitive calcium channel," *J.Biol.Chem.*, 262(25): 11904–11907 (1987).

Barhanin, et al., "The calcium channel antagonists receptor from rabbit skeletal muscle: reconstitution after purification and subunit characterization," *Eur.J.Biochem.*, 164: 525–531 (1987).

Sieber, et al., "The 165–kDa peptide of the purified skeletal muscle dihydropyridine receptor contains the (List continued on next page.)

*Primary Examiner*—Mindy B. Fleisher
*Attorney, Agent, or Firm*—Brown, Martin, Haller & McClain

[57] ABSTRACT

Calcium channel γ-subunit-encoding cDNAs, and related compositions and methods, are provided.

6 Claims, 53 Drawing Sheets

OTHER PUBLICATIONS known regulatory sites of the calcium channel," *Eur.J-.Biochem.*, 167: 117-122 (1987).

Lang, et al., "The effect of myasthenic syndrome antibody on presynaptic calcium channels in the mouse," *J.Physiol.*, 390: 257-270 (1987).

Leung, et al, "Monoclonal antibody characterization of the 1,4-dihydropyridine receptor of rabbit skeletal muscle," *Ann.N.Y.Acad.Sci.*, 522: 43-46 (1988).

Vaghy, et al., "Mechanism of action of calcium channel modulator drugs," *Ann.N.Y.Acad.Sci.*, 522: 176-186 (1988).

Noda, et al., "Existence of distinct sodium channel messager RNAs in rat brain," *Nature*, 320: 188-192 (1986).

Noda et al., "Expression of functional sodium channels from cloned cDNA," *Nature*, 322: 826-828 (1986).

Mierendorf, et al., "Gene isolation by screening kgtll libraries with antibodies," *Methods in Enz.*, 152: 458-469 (1986).

Gustin et al., "Ion channels in yeast," *Science*, 233: 1195-1197 (1986).

Curtis, et al., "Purification fo the calcium antagonist receptor of the voltage-sensitive calcium channel form skeletal muscle transverse tubules," *Biochemistry*, 23(10): 2113-2118 (1984).

Striessnig, et al., "Photoaffinity labelling of the phenylalkylamine receptor of the skeletal muscle transverse-tubule calcium channel," *FEBS Letters*, 212(2):247-253 (1987).

Borsotto, et al., "The 1,4-dihydropyridine receptor associated with the skeletal muscle voltage-dependent $Ca^{2+}$ channel," *J. Biol. Chem.*, 260(26): 14255-14263 (1985).

Cooper, et al., "Purification and characterization of the dihydropyridine-sensitive voltage-dependent calcium channel from cardiac tissue," *J.Biol.Chem.*, 262(2): 509-512 (1987).

Schmid, et al., "Immunochemical analysis of subunit structure of 1,4-dihydropyridine receptors associated with voltage-dependent $Ca^{2+}$ channels in skeletal, cardiac, and smooth muscles," *Biochemistry*, 25: 3492-3495 (1986).

Hubbard, et al., "Synthesis and processing of asparagine-linked oligosaccharides[1,2]," *Ann.Rev. Biochem.*, 50:555-583 (1981).

Breitbart et al., "Alternative Splicing: A Ubiquitous Mechanism for the Generation of Multiple Protein Isoforms From Single Genes", *Ann.Rev.Biochem.* 56:467-495 (1984).

Hamill, et al., "Improved patch-clamp techniques for high-resolution current recording from cells and cell--free membrane patches," *Pfluger Archiv.European Journal of Physiology*, 391: 85-100 (1981).

Hess, et al., "Different modes of Ca channel gating behavior favored by dihydropyridine Ca agonist and antagonists," *Nature*, 311: 538-544 (1984).

Leung, et al., "Biochemical and ultrastructural characterization of the 1,4-dihydropyridine receptor from rabbit skeletal muscle," *J. of Biol.Chem.*, 263(2): 994-1001 (1988).

Imagawa, et al., "Phosphorylation of the 1,4-dihydropyridine receptor of the voltage-dependent $Ca^{2+}$ channel by an intrinsic protein kinase in isolated triads from rabbit skeletal muscle," *J. of Biol.Chem.*, 262(17): 8333-8339 (1987).

Miller, "Multiple calcium channels and neuronal function," *Science*, 235: 46-52 (1987).

Sher, et al., "w-Conotoxin binding and effects on calcium channel function in human neuroblastoma and rat pheochromocytoma cell lines," *FEBS Letters*, 235: (1,2): 178-182 (1988).

Jay, et al., "Structural characterization of the dihydropyridine-sensitive calcium channel $\alpha_2$-subunit and the associated $\delta$ peptides," *J.Biol. Chem.*, 266(5): 3287-3293 (1991).

Ellis et al. (1988) "Sequence and Expression of mRNAs Encoding the $\alpha_1$ and $\alpha_2$ Subunits of a DHP-Sensitive Calcium Channel", *Science* 241:1661-1664.

Lotan, et al., "Specific block of calcium channel expression by a fragment of dihydropyridine receptor cDNA," *Science*, 243: 666-669 (1989).

Takahashi, et al., "Identification of an $\alpha$ subunit of dihydropyridine-sensitive brain calcium channels," *Science*, 236: 88-91 (1987).

Hofmann, et al., "Regulation of the L-type calcium channel," *TINS*, 8: 393-398 (1987).

Curtis, et al., "Reconstitution of the voltage-sensitive calcium channel purified from skeletal muscle transverse tubules," *Biochemistry*, 25: 3077-3083 (1986).

(List continued on next page.)

OTHER PUBLICATIONS

Smith, et al., "Calcium channel activity in a purified dihydropyridine-receptor preparation of skeletal muscle," *Biochemistry,* 26: 7182-7188 (1987).

Bean et al., "Classes of calcium channels in vertebrate cells," *Annu.Rev. Physiol., 51: 367-384 (1989).*

Ruth, et al., "Primary structure of the α subunit of the DHP-sensitive calcium channel from skeletal muscle," *Science,* 245: 1115-1118 (1989).

Mikami, et al., "Primary structure and functional expression of the cardiac dihydropyridine-sensitive calcium channel," *Nature, 340: 230-233 (1989).*

Biel, et al., "Primary structure and functional expression of a high voltage activiated calcium channel from rabbit lung," *FEBS Letters,* 269(2): 409-412 (1990). CHECK.

Snutch, et al., "Rat brain expresses a heterogeneous family of calcium channels," *Proc.Natl.Acad.Sci. USA,* 87: 3391-3395 (1990). CHECK.

Burns, et al., "Calcium channel activity of purified human synexin and structure of the human synexin gene," *Proc.Natl.Acad.Sci.,* 86: 3798-3802 (1989).

Campbell, et al., "32,000-Dalton subunit of the 1,4-dihydropyridine receptor," *Ann.N.Y.Acad.Sci.,* 560: 251-257 (1989). CHECK.

Dascal, N., "The use of Xenopus oocytes for the study of ion channels," *CRC Critical Rev.Biochem.,* 22(4): 317-387 (1987).

Jay, et al., "Primary Structure of the y subunit of the DHP-sensitive calcium channel from skeletal muscle," *Science,* 248: 490-492 (1990).

Cruz et al., "Characterization of ω -Conotoxin Target. Evidence for Tissue-Specific Heterogeneity ion Calcium Channel Types", *Biochem. J.* 26:820 (1987).

Carbone, et al., "Ca currents in human neuroblastoma IMR32 cells: kinetics, permeability and pharmacology," *Pfluegers Arch.* 416: 170-179 (1990) (best available copy submitted).

Dascal, et al., "Expression of modulation of voltage-gated calcium channels after RNA injection in *Xenopus* oocytes," *Science,* 231: 1147-1150 (1986).

Hess et al. "Calcium channels in vertebrate cells," *Ann.Rev.Neurosci.,* 13: 337-356 (1990).

Claudio, T., "Stable expression of transfected *Torpedo* acetylcholine receptor α subunits in mouse fibroblast L cells," *Proc. Natl.Acad.Sci.,* 84: 5967-5971 (1987).

Seagar, et al., "Molecular properties of dehydropyrine-sensitive calcium channels," *Ann.N.Y.Acad.Sci.,* 552: 162-175 (1988).

Takahashi and Catterall, "Dihydropyridine-sensitive calcium channels in cardiac and skeletal muscle membranes: studies with antibodies against the α-subunits," *Biochemistry,* 26(17): 1518-1526 (1987).

FIG. 1(a)-1

```
GCGCCGCCGC CAGACCCTAC CTGGAGCACC CACCCCTCTG CAGCCGCC                48

ATG TCC CCG ACG GAA GCC CCA AAG GTC CGC GTG ACC CTC TTC TGC ATC     96
Met Ser Pro Thr Glu Ala Pro Lys Val Arg Val Thr Leu Phe Cys Ile
 1               5                  10                  15

CTG GTG GGC ATC GTG CTG GCC ATG ACG GCC GTG GTG AGC GAC CAC TGG    144
Leu Val Gly Ile Val Leu Ala Met Thr Ala Val Val Ser Asp His Trp
            20                  25                  30

GCC GTG CTG AGC CCC CAC ATG GAG AAC CAC AAC ACC ACC TGC GAG GCC    192
Ala Val Leu Ser Pro His Met Glu Asn His Asn Thr Thr Cys Glu Ala
        35                  40                  45

GCC CAC TTC GGC CTG TGG CGG ATT TGC ACC AAG CGC ATC GCC CTG GGC    240
Ala His Phe Gly Leu Trp Arg Ile Cys Thr Lys Arg Ile Ala Leu Gly
    50                  55                  60

GAG GAC AGG AGC TGC GGA CCC ATC ACC CTG CCT GGG GAG AAG AAC TGC    288
Glu Asp Arg Ser Cys Gly Pro Ile Thr Leu Pro Gly Glu Lys Asn Cys
 65                  70                  75                  80

TCC TAC TTC CGG CAT TTT AAC CCA GGC GAG AGC TCG GAG ATC TTC GAA    336
Ser Tyr Phe Arg His Phe Asn Pro Gly Glu Ser Ser Glu Ile Phe Glu
                 85                  90                  95
```

```
TTC ACC ACG CAG AAG GAG TAC AGC ATC TCG GCG GCC GCC ATC AGC GTC      384
Phe Thr Thr Gln Lys Glu Tyr Ser Ile Ser Ala Ala Ala Ile Ser Val
            100                 105                 110

TTC AGC CTG GGC TTC CTC ATC ATG GGC ACC ATC TGC GCG CTC ATG GCC      432
Phe Ser Leu Gly Phe Leu Ile Met Gly Thr Ile Cys Ala Leu Met Ala
        115                 120                 125

TTC AGG AAG AAG CGG GAT TAC CTG CTG CGG CCG GCG TCC ATG TTC TAC      480
Phe Arg Lys Lys Arg Asp Tyr Leu Leu Arg Pro Ala Ser Met Phe Tyr
    130                 135                 140

GTC TTT GCA GGC CTC TGC CTC TTC GTG TCA CTG GAG GTA ATG CGG CAG      528
Val Phe Ala Gly Leu Cys Leu Phe Val Ser Leu Glu Val Met Arg Gln
145                 150                 155                 160

TCG GTG AAA CGC ATG ATC GAC AGC GAG GAC ACC GTC TGG ATC GAG TAC      576
Ser Val Lys Arg Met Ile Asp Ser Glu Asp Thr Val Trp Ile Glu Tyr
                165                 170                 175

TAT TAC TCC TGG TCC TTT GCC TGC GCC TGC GCC GCC TTC GTC CTC CTC      624
Tyr Tyr Ser Trp Ser Phe Ala Cys Ala Cys Ala Ala Phe Val Leu Leu
            180                 185                 190
```

FIG. 1(a)-2

```
TTC CTC GGG GGT ATC TCC CTG CTG CTC TTC TCC CTG CCT CGA ATG CCC      672
Phe Leu Gly Gly Ile Ser Leu Leu Leu Phe Ser Leu Pro Arg Met Pro
        195                 200                 205

CAG AAC CCC TGG GAG TCC TGC ATG GAC GCC GAA CCC GAG CAT TAG          717
Gln Asn Pro Trp Glu Ser Cys Met Asp Ala Glu Pro Glu His End
    210                 215                 220

CCCTCCTGGG GCGCCCAGGG AGCCTCGGCC CAGAACCTTC CAGAAGGGAG GCAGGAATTG    777

CAAACCTGCC CTGTTCCCAT CTGCCTCACC CCGCGACTGC TTCCCTTCCG TGGCTCTGAC    837

GGAGCTCCTC TGCTCACAGG GCAAATGGAC GCGAGCCCAG CCCTGTCCTG GTTGGACGAG    897

GTGGGCAGGT GGTTGGAGGG GCCCGGCCTT CCACTGAGGC TCAAAGCCGT CCCTGCTGTG    957

CCGGTTCTCC TTGGGAAGCT GGGCCCTGGT AAACCTGGTA AACCTCCCAG GAGCACCCCG   1017

TGCGCGCATG CCGGTGCTGG GTGCCCCCTG TGTGAAAAGC CGGCCCCTCT GTCTTCCCAG   1077

CCACCAGAAC CTTCGTTGCC TCCCGGAGCT CTGGGAATCA GCATTTTCCA CCAGGGAGTA   1137

TCTGACTGTG GTTTGAAATA AAAGCGCTCA GAAC                               1171
```

```
GGCTGCGCTG CGCCGCCCTC GGCTCCGACG GGCTTCTCCC ATGCGCTGAG GGCGCCGGCG      60

GGGCGTGGCG GCCGGAGGAG AGGCTCCCCT CC                                    92

ATG GTC CAG AAG ACC AGC ATG TCC CGG GGT CCT TAC CCA CCC TCC CAG       140
Met Val Gln Lys Thr Ser Met Ser Arg Gly Pro Tyr Pro Pro Ser Gln
  1               5                  10                  15

GAG ATC CCC ATG GAG GTC TTC GAC CCC AGC CCG CAG GGC AAA TAC AGC       188
Glu Ile Pro Met Glu Val Phe Asp Pro Ser Pro Gln Gly Lys Tyr Ser
             20                  25                  30

AAG AGA AAA GGG CGC TTC AAA CGG TCC GAC GGG AGC ACC TCC TCA GAT       236
Lys Arg Lys Gly Arg Phe Lys Arg Ser Asp Gly Ser Thr Ser Ser Asp
         35                  40                  45

ACA ACA TCC AAC AGC TTT GTG CGC CAG GGC TCT GCC GAG TCC TAC ACC       284
Thr Thr Ser Asn Ser Phe Val Arg Gln Gly Ser Ala Glu Ser Tyr Thr
     50                  55                  60

AGC CGT CCG TCG GAC TCT GAT GTC TCC CTG GAG GAG GAC CGG GAA GCC       332
Ser Arg Pro Ser Asp Ser Asp Val Ser Leu Glu Glu Asp Arg Glu Ala
65                  70                  75                  80

TTA AGG AAG GAA GCA GAG CGC CAG GCA TTA GCC CAG CTT GAG AAA GCC       380
Leu Arg Lys Glu Ala Glu Arg Gln Ala Leu Ala Gln Leu Glu Lys Ala
                 85                  90                  95
```

```
AAG ACC AAG CCA GTA GCA TTT GCC GTG CGG ACA AAT GTC GGC TAC AAT    428
Lys Thr Lys Pro Val Ala Phe Ala Val Arg Thr Asn Val Gly Tyr Asn
            100                 105                 110

CCA TCT CCA GGG GAT GAG GTG CCT GTG GAG GGA GTG GCC ATC ACC TTT    476
Pro Ser Pro Gly Asp Glu Val Pro Val Glu Gly Val Ala Ile Thr Phe
        115                 120                 125

GAG CCC AAG GAC TTC CTG CAC ATC AAG GAG AAA TAC AAC AAT GAC TGG    524
Glu Pro Lys Asp Phe Leu His Ile Lys Glu Lys Tyr Asn Asn Asp Trp
    130                 135                 140

TGG ATT GGG CGG CTG GTG AAG GAG GGC TGC GAG GTT GGC TTC ATC CCC    572
Trp Ile Gly Arg Leu Val Lys Glu Gly Cys Glu Val Gly Phe Ile Pro
145                 150                 155                 160

AGC CCC GTC AAA CTG GAC AGC CTG CGC CTG CTG CAG GAA CAG AAG CTG    620
Ser Pro Val Lys Leu Asp Ser Leu Arg Leu Leu Gln Glu Gln Lys Leu
                165                 170                 175

CGT CAG AGC CGC CTC AGC TCC AGC AAA TCA GGC GAC AAC TCC AGC TCC    668
Arg Gln Ser Arg Leu Ser Ser Ser Lys Ser Gly Asp Asn Ser Ser Ser
            180                 185                 190
```

```
AGT CTG GGT GAC GTA GTG ACT GGC ACG CGC CGC CCC ACA CCC CCT GCC     716
Ser Leu Gly Asp Val Val Thr Gly Thr Arg Arg Pro Thr Pro Pro Ala
        195                 200                 205

AGT GGT AAC GAG ATG ACT AAC TTA GCC TTT GAA CTA GAG CCC TTA GAC     764
Ser Gly Asn Glu Met Thr Asn Leu Ala Phe Glu Leu Glu Pro Leu Asp
    210                 215                 220

TTA GAG GAG GAC GAG GCA GAG CTC GGT GAG CAG AGC GGC TCT GCC AAG     812
Leu Glu Glu Asp Glu Ala Glu Leu Gly Glu Gln Ser Gly Ser Ala Lys
225                 230                 235                 240

ACT AGC GTT AGC AGT GTC ACC ACC CCG CCA CCC CAC GGC ACA CGC ATC     860
Thr Ser Val Ser Ser Val Thr Thr Pro Pro Pro His Gly Thr Arg Ile
                245                 250                 255

CCC TTC TTT AAG AAG ACA GAG CAC GTG CCC CCC TAT GAC GTG GTG CCT     908
Pro Phe Phe Lys Lys Thr Glu His Val Pro Pro Tyr Asp Val Val Pro
            260                 265                 270

TCC ATG AGG CCC ATC ATC CTG GTG GGA CCG TCG CTC AAG GGC TAT GAG     956
Ser Met Arg Pro Ile Ile Leu Val Gly Pro Ser Leu Lys Gly Tyr Glu
        275                 280                 285

GTG ACA GAC ATG ATG CAG AAA GCT TTG TTT GAC TTC CTG AAG CAT CGG    1004
Val Thr Asp Met Met Gln Lys Ala Leu Phe Asp Phe Leu Lys His Arg
    290                 295                 300
```

```
TTT GAT GGC AGG ATC TCC ATC ACg CGG GTG ACA GCC GAC ATC TCC CTG     1052
Phe Asp Gly Arg Ile Ser Ile Thr Arg Val Thr Ala Asp Ile Ser Leu
305                 310                 315                 320

GCT AAG CGC TCA GTC CTC AAC AAC CCC AGC AAG CAC ATC ATC ATC GAG     1100
Ala Lys Arg Ser Val Leu Asn Asn Pro Ser Lys His Ile Ile Ile Glu
                325                 330                 335

CGC TCC AAC ACA CGC TCC AGC CTG GCT GAG GTG CAG AGT GAG ATT GAA     1148
Arg Ser Asn Thr Arg Ser Ser Leu Ala Glu Val Gln Ser Glu Ile Glu
            340                 345                 350

CGA ATC TTC GAG CTG GCC CGG ACC CTC CAG CTG GTC GCT CTG GAC GCG     1196
Arg Ile Phe Glu Leu Ala Arg Thr Leu Gln Leu Val Ala Leu Asp Ala
        355                 360                 365

GAC ACC ATC AAC CAC CCT GCC CAG CTC TCC AAG ACC TCA CTG GCG CCC     1244
Asp Thr Ile Asn His Pro Ala Gln Leu Ser Lys Thr Ser Leu Ala Pro
    370                 375                 380

ATC ATT GTT TAC ATC AAG ATC ACC TCC CCC AAG GTA CTT CAG AGG CTC     1292
Ile Ile Val Tyr Ile Lys Ile Thr Ser Pro Lys Val Leu Gln Arg Leu
385                 400                 405                 500
```

FIG. 4(b)-2

```
ATC AAG TCC CGG GGG AAG TCT CAG TCC AAA CAC CTC AAC GTC CAG ATA   1340
Ile Lys Ser Arg Gly Lys Ser Gln Ser Lys His Leu Asn Val Gln Ile
                505                 510                 515
GCA GCC TCG GAG AAG CTG GCG CAG TGT CCG CCC GAA ATG TTT GAC ATC   1388
Ala Ala Ser Glu Lys Leu Ala Gln Cys Pro Pro Glu Met Phe Asp Ile
            520                 525                 530
ATC CTG GAC GAG AAC CAA TTG GAG GAT GCC TGC GAG CAC CTG GCC GAG   1436
Ile Leu Asp Glu Asn Gln Leu Glu Asp Ala Cys Glu His Leu Ala Glu
        535                 540                 545

TAC TTG GAA GCC TAC TGG AAG GCC ACA CAC CCG CCC AGC AGC ACA CCG   1484
Tyr Leu Glu Ala Tyr Trp Lys Ala Thr His Pro Pro Ser Ser Thr Pro
    550                 555                 560

CCC AAT CCG CTG CTG AAC CGC ACC ATG GCC ACC GCA GCC CTG GCC GCC   1532
Pro Asn Pro Leu Leu Asn Arg Thr Met Ala Thr Ala Ala Leu Ala Ala
565                 570                 575                 580

AGC CCT GCC CCT GTC TCC AAC CTC CAG GTA CAG GTG CTC ACC TCG CTC   1580
Ser Pro Ala Pro Val Ser Asn Leu Gln Val Gln Val Leu Thr Ser Leu
                585                 590                 595

AGG AGA AAC CTC AGC TTC TGG GGC GGG CTG GAG ACC TCC CAG CGG GGC   1628
Arg Arg Asn Leu Ser Phe Trp Gly Gly Leu Glu Thr Ser Gln Arg Gly
            600                 605                 610

GGC GGT GCG GTG CCC CAA CAG CAG GAG CAC GCC ATG TAG               1667
Gly Gly Ala Val Pro Gln Gln Gln Glu His Ala Met End
CGGGGGACCG CCCGTCTTCC CTCCGCCCAG GGCGTGGAAC TGGAGTGCAG GGAACATGGG 1727

CAAGGAAGGG AAGAGCTTTA TTTTGTAAAA AACGTGGTGA GCGGC                 1772
```

```
GCGGGGAACA CTGGGGACGC AGGGAAGAGA GGGCCGCGGG GTGGGGGAGC AGCAGGAAGC     60

GCCGTGGCCA GGGAAGCC                                                   78

ATG GAG CCA TCC TCA CCC CAG GAT GAG GGC CTG AGG AAG AAA CAG CCC     126
Met Glu Pro Ser Ser Pro Gln Asp Glu Gly Leu Arg Lys Lys Gln Pro
  1               5                  10                  15

AAG AAG CCC CTG CCC GAG GTC CTG CCC AGG CCG CCG CGG GCT CTG TTC     174
Lys Lys Pro Leu Pro Glu Val Leu Pro Arg Pro Pro Arg Ala Leu Phe
             20                  25                  30

TGC CTG ACC CTG CAG AAC CCG CTG AGG AAG GCG TGC ATC AGC ATC GTG     222
Cys Leu Thr Leu Gln Asn Pro Leu Arg Lys Ala Cys Ile Ser Ile Val
         35                  40                  45

GAA TGG AAA CCC TTC GAG ACC ATC ATC CTG CTC ACC ATC TTT GCC AAC     270
Glu Trp Lys Pro Phe Glu Thr Ile Ile Leu Leu Thr Ile Phe Ala Asn
     50                  55                  60

TGT GTG GCC CTG GCC GTG TAC CTG CCC ATG CCC GAG GAT GAC AAC AAC     318
Cys Val Ala Leu Ala Val Tyr Leu Pro Met Pro Glu Asp Asp Asn Asn
65                   70                  75                  80

TCC CTG AAC CTG GGC CTG GAG AAG CTG GAG TAC TTC TTC CTC ACC GTC     366
Ser Leu Asn Leu Gly Leu Glu Lys Leu Glu Tyr Phe Phe Leu Thr Val
                 85                  90                  95
```

```
TTC TCC ATC GAA GCC GCC ATG AAG ATC ATC GCC TAC GGC TTC CTG TTC     414
Phe Ser Ile Glu Ala Ala Met Lys Ile Ile Ala Tyr Gly Phe Leu Phe
            100                 105                 110

CAC CAG GAC GCC TAC CTG CGC AGC GGC TGG AAC GTG CTG GAC TTC ATC     462
His Gln Asp Ala Tyr Leu Arg Ser Gly Trp Asn Val Leu Asp Phe Ile
        115                 120                 125

ATC GTC TTC CTG GGG GTC TTC ACG GCG ATT CTG GAA CAG GTC AAC GTC     510
Ile Val Phe Leu Gly Val Phe Thr Ala Ile Leu Glu Gln Val Asn Val
    130                 135                 140

ATC CAG AGC AAC ACG GCC CCG ATG AGC AGC AAA GGA GCC GGC CTG GAC     558
Ile Gln Ser Asn Thr Ala Pro Met Ser Ser Lys Gly Ala Gly Leu Asp
145                 150                 155                 160

GTC AAG GCC CTG AGG GCC TTC CGT GTG CTC AGA CCC CTC CGG CTG GTG     606
Val Lys Ala Leu Arg Ala Phe Arg Val Leu Arg Pro Leu Arg Leu Val
                165                 170                 175

TCG GGG GTG CCT AGT TTG CAG GTG GTC CTC AAC TCC ATC TTC AAG GCC     654
Ser Gly Val Pro Ser Leu Gln Val Val Leu Asn Ser Ile Phe Lys Ala
            180                 185                 190
```

```
ATG CTC CCC CTG TTC CAC ATC GCC CTG CTC GTC CTC TTC ATG GTC ATC     702
Met Leu Pro Leu Phe His Ile Ala Leu Leu Val Leu Phe Met Val Ile
        195                 200                     205

ATC TAC GCC ATC ATC GGG CTG GAG CTC TTC AAG GGC AAG ATG CAC AAG     750
Ile Tyr Ala Ile Ile Gly Leu Glu Leu Phe Lys Gly Lys Met His Lys
    210                 215                     220

ACC TGC TAC TAC ATC GGG ACA GAC ATC GTG GCC ACA GTG GAG AAT GAG     798
Thr Cys Tyr Tyr Ile Gly Thr Asp Ile Val Ala Thr Val Glu Asn Glu
225                     230                     235                 240

AAG CCC TCG CCC TGC GCT AGG ACG GGC TCG GGG CGC CCC TGC ACC ATC     846
Lys Pro Ser Pro Cys Ala Arg Thr Gly Ser Gly Arg Pro Cys Thr Ile
                245                     250                     255

AAC GGC AGC GAG TGC CGG GGC GGC TGG CCG GGG CCC AAC CAC GGC ATC     894
Asn Gly Ser Glu Cys Arg Gly Gly Trp Pro Gly Pro Asn His Gly Ile
            260                     265                     270

ACG CAC TTC GAC AAC TTC GGC TTC TCC ATG CTC ACC GTG TAC CAG TGC     942
Thr His Phe Asp Asn Phe Gly Phe Ser Met Leu Thr Val Tyr Gln Cys
        275                     280                     285

ATC ACC ATG GAG GGC TGG ACA GAT GTC CTC TAC TGG GTC AAC GAT GCC     990
Ile Thr Met Glu Gly Trp Thr Asp Val Leu Tyr Trp Val Asn Asp Ala
    290                     295                     300
```

```
ATC GGG AAC GAG TGG CCC TGG ATC TAC TTT GTC ACT CTC ATC CTG CTG     1038
Ile Gly Asn Glu Trp Pro Trp Ile Tyr Phe Val Thr Leu Ile Leu Leu
305                 310                 315                 320

GGG TCC TTC TTC ATC CTC AAC CTG GTG CTG GGC GTC CTG AGT GGG GAA     1086
Gly Ser Phe Phe Ile Leu Asn Leu Val Leu Gly Val Leu Ser Gly Glu
                325                 330                 335

TTC ACC AAG GAG CGG GAG AAG GCC AAG TCC AGG GGA ACC TTC CAG AAG     1134
Phe Thr Lys Glu Arg Glu Lys Ala Lys Ser Arg Gly Thr Phe Gln Lys
            340                 345                 350

CTG CGG GAG AAG CAG CAG CTG GAG GAG GAC CTT CGG GGC TAC ATG AGC     1182
Leu Arg Glu Lys Gln Gln Leu Glu Glu Asp Leu Arg Gly Tyr Met Ser
        355                 360                 365

TGG ATC ACG CAG GGC GAG GTC ATG GAC GTG GAG GAC CTG AGA GAA GGA     1230
Trp Ile Thr Gln Gly Glu Val Met Asp Val Glu Asp Leu Arg Glu Gly
    370                 375                 380

AAG CTG TCC TTG GAA GAG GGA GGC TCC GAC ACG GAA AGC CTG TAC GAA     1278
Lys Leu Ser Leu Glu Glu Gly Gly Ser Asp Thr Glu Ser Leu Tyr Glu
385                 390                 395                 400
```

```
ATC GAG GGC TTG AAC AAA ATC ATC CAG TTC ATC CGA CAC TGG AGG CAG    1326
Ile Glu Gly Leu Asn Lys Ile Ile Gln Phe Ile Arg His Trp Arg Gln
                405                 410                 415

TGG AAC CGT GTC TTT CGC TGG AAG TGC CAT GAC CTG GTG AAG TCG AGA    1374
Trp Asn Arg Val Phe Arg Trp Lys Cys His Asp Leu Val Lys Ser Arg
            420                 425                 430

GTC TTC TAC TGG CTG GTC ATC CTG ATC GTG GCC CTC AAC ACC CTG TCC    1422
Val Phe Tyr Trp Leu Val Ile Leu Ile Val Ala Leu Asn Thr Leu Ser
        435                 440                 445

ATC GCC TCG GAG CAC CAC AAC CAG CCG CTC TGG CTG ACC CAC TTG CAA    1470
Ile Ala Ser Glu His His Asn Gln Pro Leu Trp Leu Thr His Leu Gln
    450                 455                 460

GAC ATC GCC AAT CGA GTG CTG CTG TCA CTC TTC ACC ATC GAG ATG CTG    1518
Asp Ile Ala Asn Arg Val Leu Leu Ser Leu Phe Thr Ile Glu Met Leu
465                 470                 475                 480

CTG AAG ATG TAC GGG CTG GGC CTG CGC CAG TAC TTC ATG TCC ATC TTC    1566
Leu Lys Met Tyr Gly Leu Gly Leu Arg Gln Tyr Phe Met Ser Ile Phe
                485                 490                 495

AAC CGC TTC GAC TGC TTC GTG GTG TGC AGC GGC ATC CTG GAG CTG CTG    1614
Asn Arg Phe Asp Cys Phe Val Val Cys Ser Gly Ile Leu Glu Leu Leu
            500                 505                 510
```

```
CTG GTG GAG TCG GGC GCC ATG ACG CCG CTG GGC ATC TCC GTG TTG CGC      1662
Leu Val Glu Ser Gly Ala Met Thr Pro Leu Gly Ile Ser Val Leu Arg
        515                 520                 525

TGC ATC CGC CTC CTG AGG CTC TTC AAG ATC ACC AAG TAC TGG ACG TCG      1710
Cys Ile Arg Leu Leu Arg Leu Phe Lys Ile Thr Lys Tyr Trp Thr Ser
    530                 535                 540

CTC AGC AAC CTG GTG GCC TCC CTG CTC AAC TCC ATC CGC TCC ATC GCC      1758
Leu Ser Asn Leu Val Ala Ser Leu Leu Asn Ser Ile Arg Ser Ile Ala
545                 550                 555                 560

TCG CTG CTG CTG CTG CTC TTC CTC TTC ATC ATC ATC TTC GCC CTG CTG      1806
Ser Leu Leu Leu Leu Leu Phe Leu Phe Ile Ile Ile Phe Ala Leu Leu
                565                 570                 575

GGC ATG CAG CTC TTC GGG GGG CGG TAC GAC TTC GAG GAC ACG GAA GTG      1854
Gly Met Gln Leu Phe Gly Gly Arg Tyr Asp Phe Glu Asp Thr Glu Val
            580                 585                 590

CGA CGC AGC AAC TTC GAC AAC TTC CCC CAG GCC CTC ATC AGC GTC TTC      1902
Arg Arg Ser Asn Phe Asp Asn Phe Pro Gln Ala Leu Ile Ser Val Phe
        595                 600                 605
```

```
CAG GTG CTG ACG GGT GAG GAC TGG AAC TCC GTG ATG TAC AAC GGG ATC    1950
Gln Val Leu Thr Gly Glu Asp Trp Asn Ser Val Met Tyr Asn Gly Ile
    610                 615                 620

ATG GCC TAC GGA GGC CCG TCC TAC CCG GGC GTT CTC GTG TGC ATC TAT    1998
Met Ala Tyr Gly Gly Pro Ser Tyr Pro Gly Val Leu Val Cys Ile Tyr
625                 630                 635                 640

TTC ATC ATC CTT TTT GTC TGC GGC AAC TAT ATC CTG CTG AAT GTC TTC    2046
Phe Ile Ile Leu Phe Val Cys Gly Asn Tyr Ile Leu Leu Asn Val Phe
                645                 650                 655

CTG GCC ATC GCC GTG GAC AAC CTG GCC GAG GCC GAG AGC CTG ACT TCC    2094
Leu Ala Ile Ala Val Asp Asn Leu Ala Glu Ala Glu Ser Leu Thr Ser
            660                 665                 670

GCG CAA AAG GCC AAG GCC GAG GAG AGG AAA CGT AGG AAG ATG TCC AGG    2142
Ala Gln Lys Ala Lys Ala Glu Glu Arg Lys Arg Arg Lys Met Ser Arg
        675                 680                 685     (P)

GGT CTC CCT GAC AAG ACG GAG GAG GAG AAG TCT GTG ATG GCC AAG AAG    2190
Gly Leu Pro Asp Lys Thr Glu Glu Glu Lys Ser Val Met Ala Lys Lys
    690                 695                 700

CTG GAG CAG AAG CCC AAG GGG GAG GGC ATC CCC ACC ACT GCC AAG CTC    2238
Leu Glu Gln Lys Pro Lys Gly Glu Gly Ile Pro Thr Thr Ala Lys Leu
705                 710                 715                 720
```

```
AAG GTC GAT GAG TTC GAA TCT AAC GTC AAC GAG GTG AAG GAC CCC TAC    2286
Lys Val Asp Glu Phe Glu Ser Asn Val Asn Glu Val Lys Asp Pro Tyr
                725                 730                 735

CCT TCA GCT GAC TTC CCA GGG GAT GAT GAG GAG GAC GAG CCT GAG ATC    2334
Pro Ser Ala Asp Phe Pro Gly Asp Asp Glu Glu Asp Glu Pro Glu Ile
            740                 745                 750

CCA GTG AGC CCC CGA CCG CGC CCG CTG GCC GAG CTG CAG CTC AAA GAG    2382
Pro Val Ser Pro Arg Pro Arg Pro Leu Ala Glu Leu Gln Leu Lys Glu
        755                 760                 765

AAG GCA GTG CCC ATC CCG GAA GCC AGC TCC TTC TTC ATC TTC AGT CCC    2430
Lys Ala Val Pro Ile Pro Glu Ala Ser Ser Phe Phe Ile Phe Ser Pro
    770                 775                 780

ACC AAT AAG GTC CGT GTC CTG TGT CAC CGC ATC GTC AAC GCC ACC TGG    2478
Thr Asn Lys Val Arg Val Leu Cys His Arg Ile Val Asn Ala Thr Trp
785                 790                 795      •              800

TTC ACC AAC TTC ATC CTG CTC TTC ATC CTG CTC AGC AGT GCT GCG CTG    2526
Phe Thr Asn Phe Ile Leu Leu Phe Ile Leu Leu Ser Ser Ala Ala Leu
                805                 810                 815
```

```
GCC GCC GAG GAC CCC ATC CGG GCG GAG TCC GTG AGG AAT CAG ATC CTT    2574
Ala Ala Glu Asp Pro Ile Arg Ala Glu Ser Val Arg Asn Gln Ile Leu
            820                 825                 830

GGA TAT TTT GAT ATT GCC TTC ACC TCT GTC TTC ACT GTG GAG ATT GTC    2622
Gly Tyr Phe Asp Ile Ala Phe Thr Ser Val Phe Thr Val Glu Ile Val
        835                 840                 845

CTC AAG ATG ACA ACC TAC GGC GCC TTC CTG CAC AAG GGC TCC TTC TGC    2670
Leu Lys Met Thr Thr Tyr Gly Ala Phe Leu His Lys Gly Ser Phe Cys
    850                 855                 860

CGC AAC TAC TTC AAC ATC CTG GAC CTG CTG GTG GTG GCC GTG TCT CTC    2718
Arg Asn Tyr Phe Asn Ile Leu Asp Leu Leu Val Val Ala Val Ser Leu
865                 870                 875                 880

ATC TCC ATG GGT CTC GAG TCC AGC ACC ATC TCC GTG GTA AAG ATC CTG    2766
Ile Ser Met Gly Leu Glu Ser Ser Thr Ile Ser Val Val Lys Ile Leu
                885                 890                 895

AGA GTG CTA AGG GTG CTC CGG CCC CTG CGA GCC ATC AAC AGA GCC AAA    2814
Arg Val Leu Arg Val Leu Arg Pro Leu Arg Ala Ile Asn Arg Ala Lys
            900                 905                 910

GGG TTG AAG CAC GTG GTC CAG TGC GTG TTC GTG GCC ATC CGC ACC ATC    2862
Gly Leu Lys His Val Val Gln Cys Val Phe Val Ala Ile Arg Thr Ile
        915                 920                 925
```

GGG AAC ATC GTC CTG GTC ACC ACG CTC CTG CAG TTC ATG TTC GCC TGC 2910
Gly Asn Ile Val Leu Val Thr Thr Leu Leu Gln Phe Met Phe Ala Cys
930 935 940

ATC GGT GTC CAG CTC TTC AAG GGC AAG TTC TTC AGC TGC AAT GAC CTA 2958
Ile Gly Val Gln Leu Phe Lys Gly Lys Phe Phe Ser Cys Asn Asp Leu
945 950 955 960

TCC AAG ATG ACA GAA GAG GAG TGC AGG GGC TAC TAC TAT GTG TAC AAG 3006
Ser Lys Met Thr Glu Glu Glu Cys Arg Gly Tyr Tyr Tyr Val Tyr Lys
965 970 975

GAC GGG GAC CCC ACG CAG ATG GAG CTG CGC CCC CGC CAG TGG ATA CAC 3054
Asp Gly Asp Pro Thr Gln Met Glu Leu Arg Pro Arg Gln Trp Ile His
980 985 990

AAT GAC TTC CAC TTT GAC AAC GTG CTG TCG GCC ATG ATG TCG CTC TTC 3102
Asn Asp Phe His Phe Asp Asn Val Leu Ser Ala Met Met Ser Leu Phe
995 1000 1005

ACG GTG TCC ACC TTC GAG GGA TGG CCC CAG CTG CTG TAC AGG GCC ATA 3150
Thr Val Ser Thr Phe Glu Gly Trp Pro Gln Leu Leu Tyr Arg Ala Ile
1010 1015 1020

```
GAC TCC AAC GAG GAG GAC ATG GGC CCC GTT TAC AAC AAC CGA GTG GAG   3198
Asp Ser Asn Glu Glu Asp Met Gly Pro Val Tyr Asn Asn Arg Val Glu
1025                1030                1035                1040

ATG GCC ATC TTC TTC ATC ATC TAC ATC ATC CTC ATT GCC TTC TTC ATG   3246
Met Ala Ile Phe Phe Ile Ile Tyr Ile Ile Leu Ile Ala Phe Phe Met
                1045                1050                1055

ATG AAC ATC TTT GTG GGC TTT GTC ATC GTC ACC TTC CAG GAG CAG GGG   3294
Met Asn Ile Phe Val Gly Phe Val Ile Val Thr Phe Gln Glu Gln Gly
            1060                1065                1070

GAG ACG GAG TAC AAG AAC TGC GAG CTG GAC AAG AAC CAG CGC CAG TGT   3342
Glu Thr Glu Tyr Lys Asn Cys Glu Leu Asp Lys Asn Gln Arg Gln Cys
        1075                1080                1085

GTG CAG TAT GCC CTG AAG GCC CGC CCA CTT CGG TGC TAC ATC CCC AAG   3390
Val Gln Tyr Ala Leu Lys Ala Arg Pro Leu Arg Cys Tyr Ile Pro Lys
    1090                1095                1100

AAC CCA TAC CAG TAC CAG GTG TGG TAC GTC GTC ACC TCC TCC TAC TTT   3438
Asn Pro Tyr Gln Tyr Gln Val Trp Tyr Val Val Thr Ser Ser Tyr Phe
1105                1110                1115                1120

GAA TAC CTG ATG TTC GCC CTC ATC ATG CTC AAC ACC ATC TGC CTG GGC   3486
Glu Tyr Leu Met Phe Ala Leu Ile Met Leu Asn Thr Ile Cys Leu Gly
                1125                1130                1135
```

```
ATG CAG CAC TAC CAC CAG TCG GAG GAG ATG AAC CAC ATC TCA GAC ATC     3534
Met Gln His Tyr His Gln Ser Glu Glu Met Asn His Ile Ser Asp Ile
            1140                1145                1150

CTC AAT GTG GCC TTC ACC ATC ATC TTC ACG CTG GAG ATG ATT CTC AAG     3582
Leu Asn Val Ala Phe Thr Ile Ile Phe Thr Leu Glu Met Ile Leu Lys
        1155                1160                1165

CTC TTG GCG TTC AAG GCC AGG GGC TAT TTC GGA GAC CCC TGG AAT GTG     3630
Leu Leu Ala Phe Lys Ala Arg Gly Tyr Phe Gly Asp Pro Trp Asn Val
    1170                1175                1180

TTC GAC TTC CTG ATC GTC ATC GGC AGC ATC ATT GAC GTC ATC CTC AGC     3678
Phe Asp Phe Leu Ile Val Ile Gly Ser Ile Ile Asp Val Ile Leu Ser
1185                1190                1195                1200

GAG ATC GAC ACT TTC CTG GCC TCC AGC GGG GGA CTG TAT TGC CTG GGT     3726
Glu Ile Asp Thr Phe Leu Ala Ser Ser Gly Gly Leu Tyr Cys Leu Gly
                1205                1210                1215

GGC GGC TGC GGG AAC GTT GAC CCA GAC GAG AGC GCC CGC ATC TCC AGT     3774
Gly Gly Cys Gly Asn Val Asp Pro Asp Glu Ser Ala Arg Ile Ser Ser
            1220                1225                1230
```

```
GCC TTC TTC CGC CTG TTC CGG GTT ATG AGG CTG ATC AAG CTG CTG AGT      3822
Ala Phe Phe Arg Leu Phe Arg Val Met Arg Leu Ile Lys Leu Leu Ser
        1235                1240                1245

CGG GCC GAG GGC GTG CGC ACG CTG CTG TGG ACG TTC ATC AAG TCC TTC      3870
Arg Ala Glu Gly Val Arg Thr Leu Leu Trp Thr Phe Ile Lys Ser Phe
    1250                1255                1260

CAG GCC CTG CCC TAC GTG GCC CTG CTC ATC GTC ATG CTG TTC TTC ATC      3918
Gln Ala Leu Pro Tyr Val Ala Leu Leu Ile Val Met Leu Phe Phe Ile
1265                1270                1275                1280

TAC GCC GTC ATC GGC ATG CAG ATG TTT GGA AAG ATC GCC CTG GTG GAC      3966
Tyr Ala Val Ile Gly Met Gln Met Phe Gly Lys Ile Ala Leu Val Asp
                1285                1290                1295

GGG ACC CAG ATC AAC CGC AAC AAC AAC TTC CAG ACC TTC CCG CAG GCC      4014
Gly Thr Gln Ile Asn Arg Asn Asn Asn Phe Gln Thr Phe Pro Gln Ala
            1300                1305                1310

GTG CTG CTG CTC TTC AGG TGT GCG ACA GGG GAG GCG TGG CAA GAG ATC      4062
Val Leu Leu Leu Phe Arg Cys Ala Thr Gly Glu Ala Trp Gln Glu Ile
        1315                1320                1325

CTG CTG GCC TGC AGC TAC GGG AAG TTG TGC GAC CCA GAG TCA GAC TAC      4110
Leu Leu Ala Cys Ser Tyr Gly Lys Leu Cys Asp Pro Glu Ser Asp Tyr
    1330                1335                1340
```

```
GCC CCG GGC GAG GAG TAC ACG TGT GGC ACC AAC TTC GCC TAC TAC TAC     4158
Ala Pro Gly Glu Glu Tyr Thr Cys Gly Thr Asn Phe Ala Tyr Tyr Tyr
1345                1350                1355                1360

TTC ATC AGC TTC TAC ATG CTC TGC GCC TTC CTG ATC ATC AAC CTC TTC     4206
Phe Ile Ser Phe Tyr Met Leu Cys Ala Phe Leu Ile Ile Asn Leu Phe
                1365                1370                1375

GTG GCT GTC ATC ATG GAC AAC TTT GAC TAC CTG ACA CGC GAC TGG TCC     4254
Val Ala Val Ile Met Asp Asn Phe Asp Tyr Leu Thr Arg Asp Trp Ser
            1380                1385                1390

ATC CTG GGC CCT CAC CAC CTG GAC GAG TTC AAG GCC ATC TGG GCA GAG     4302
Ile Leu Gly Pro His His Leu Asp Glu Phe Lys Ala Ile Trp Ala Glu
        1395                1400                1405

TAT GAC CCA GAG GCC AAG GGG CGA ATC AAG CAC CTG GAC GTG GTG ACC     4350
Tyr Asp Pro Glu Ala Lys Gly Arg Ile Lys His Leu Asp Val Val Thr
    1410                1415                1420

CTG CTG AGA AGG ATC CAG CCC CCT CTG GGC TTC GGG AAG TTC TGT CCA     4398
Leu Leu Arg Arg Ile Gln Pro Pro Leu Gly Phe Gly Lys Phe Cys Pro
1425                1430                1435                1440
```

```
CAC CGG GTG GCC TGT AAG CGC CTG GTG GGC ATG AAC ATG CCC CTG AAC     4446
His Arg Val Ala Cys Lys Arg Leu Val Gly Met Asn Met Pro Leu Asn
                1445                1450                1455

AGT GAC GGC ACG GTC ACC TTC AAT GCC ACG CTC TTT GCC CTG GTG CGC     4494
Ser Asp Gly Thr Val Thr Phe Asn Ala Thr Leu Phe Ala Leu Val Arg
            1460              • 1465                1470

ACG GCC CTC AAG ATC AAG ACA GAA GGT AAC TTC GAG CAG GCC AAC GAG     4542
Thr Ala Leu Lys Ile Lys Thr Glu Gly Asn Phe Glu Gln Ala Asn Glu
        1475                1480                1485

GAG CTG AGG GCC ATC ATC AAG AAG ATC TGG AAG AGA ACC AGC ATG AAG     4590
Glu Leu Arg Ala Ile Ile Lys Lys Ile Trp Lys Arg Thr Ser Met Lys
    1490                1495                1500    (P)

CTA CTG GAC CAG GTC ATC CCT CCC ATA GGA GAT GAC GAG GTG ACC GTG     4638
Leu Leu Asp Gln Val Ile Pro Pro Ile Gly Asp Asp Glu Val Thr Val
1505                1510                1515                1520

GGG AAG TTC TAC GCC ACA TTC CTC ATC CAG GAG CAC TTC CGG AAG TTC     4686
Gly Lys Phe Tyr Ala Thr Phe Leu Ile Gln Glu His Phe Arg Lys Phe
                1525                1530                1535

ATG AAG CGC CAG GAG GAA TAT TAT GGG TAT CGG CCC AAG AAG GAC ACC     4734
Met Lys Arg Gln Glu Glu Tyr Tyr Gly Tyr Arg Pro Lys Lys Asp Thr
            1540                1545                1550
```

```
GTG CAG ATC CAG GCT GGG CTG CGG ACC ATA GAG GAG GAG GCG GCC CCT     4782
Val Gln Ile Gln Ala Gly Leu Arg Thr Ile Glu Glu Glu Ala Ala Pro
        1555                1560                1565

GAG ATC CGC CGC ACC ATC TCA GGA GAC CTG ACC GCC GAG GAG GAG CTG     4830
Glu Ile Arg Arg Thr Ile Ser Gly Asp Leu Thr Ala Glu Glu Glu Leu
    1570                    (P)                 1580

GAG AGA GCC ATG GTG GAG GCT GCG ATG GAG GAG AGG ATC TTC CGG AGG     4878
Glu Arg Ala Met Val Glu Ala Ala Met Glu Glu Arg Ile Phe Arg Arg
1585                1590                1595                1600

ACC GGA GGC CTG TTT GGC CAG GTG GAC ACC TTC CTG GAA AGG ACC AAC     4926
Thr Gly Gly Leu Phe Gly Gln Val Asp Thr Phe Leu Glu Arg Thr Asn
                1605                1610                1615

TCC CTA CCC CCG GTG ATG GCC AAC CAA AGA CCG CTC CAG TTT GCT GAG     4974
Ser Leu Pro Pro Val Met Ala Asn Gln Arg Pro Leu Gln Phe Ala Glu
            1620                1625                1630

ATA GAA ATG GAA GAG CTT GAG TCG CCT GTC TTC TTG GAG GAC TTC CCT     5022
Ile Glu Met Glu Glu Leu Glu Ser Pro Val Phe Leu Glu Asp Phe Pro
        1635                1640                1645
```

```
CAA GAC GCA AGA ACC AAC CCT CTC GCT CGT GCC AAT ACC AAC AAC GCC     5070
Gln Asp Ala Arg Thr Asn Pro Leu Ala Arg Ala Asn Thr Asn Asn Ala
   1650                1655                1660

AAT GCC AAT GTT GCC TAT GGC AAC AGC AAC CAT AGC AAC AAC CAG ATG     5118
Asn Ala Asn Val Ala Tyr Gly Asn Ser Asn His Ser Asn Asn Gln Met
1665                1670                • 1675                1680

TTT TCC AGC GTC CAC TGT GAA AGG GAG TTC CCG GGA GAG GCG GAG ACA     5166
Phe Ser Ser Val His Cys Glu Arg Glu Phe Pro Gly Glu Ala Glu Thr
               1685                1690                1695

CCG GCT GCC GGA CGA GGA GCC CTC AGC CAC TCC CAC AGG GCC CTG GGA     5214
Pro Ala Ala Gly Arg Gly Ala Leu Ser His Ser His Arg Ala Leu Gly
           1700                1705                1710

CCT CAC AGC AAG CCC TGT GCT GGA AAA CTG AAT GGG CAG CTG GTC CAG     5262
Pro His Ser Lys Pro Cys Ala Gly Lys Leu Asn Gly Gln Leu Val Gln
       1715                1720                1725

CCG GGA ATG CCC ATC AAC CAG GCA CCT CCT GCC CCC TGC CAG CAG CCT     5310
Pro Gly Met Pro Ile Asn Gln Ala Pro Pro Ala Pro Cys Gln Gln Pro
   1730                1735                1740

AGC ACA GAT CCC CCA GAG CGC GGG CAG AGG AGG ACC TCC CTG ACA GGG     5358
Ser Thr Asp Pro Pro Glu Arg Gly Gln Arg Arg Thr Ser Leu Thr Gly
1745                1750                1755      (P)        1760
```

```
TCT CTG CAA GAC GAA GCA CCC CAG AGG AGG AGC TCC GAG GGG AGC ACC    5406
Ser Leu Gln Asp Glu Ala Pro Gln Arg Arg Ser Ser Glu Gly Ser Thr
                1765                    1770    (P)         1775

CCC AGG CGC CCG GCT CCT GCT ACA GCT CTG CTG ATC CAA GAG GCT CTG    5454
Pro Arg Arg Pro Ala Pro Ala Thr Ala Leu Leu Ile Gln Glu Ala Leu
            1780                    1785                    1790

GTT CGA GGG GGC CTG GAC ACC TTG GCA GCT GAT GCT GGC TTC GTC ATG    5502
Val Arg Gly Gly Leu Asp Thr Leu Ala Ala Asp Ala Gly Phe Val Met
        1795                    1800                    1805

GCA ACA AGC CAG GCC CTG GTA GAC GCC TGT CAG ATG GAA CCG GAG GAA    5550
Ala Thr Ser Gln Ala Leu Val Asp Ala Cys Gln Met Glu Pro Glu Glu
    1810                    1815                    1820

GTA GAG GTC GCA GCC ACA GAG CTA CTG AAA GAG CGA GAG TCC GTC CAG    5598
Val Glu Val Ala Ala Thr Glu Leu Leu Lys Glu Arg Glu Ser Val Gln
1825                    1830                    1835                    1840

GGC ATG GCC AGT GTC CCG GGA AGC CTG AGC CGC AGG TCC TCC CTG GGC    5646
Gly Met Ala Ser Val Pro Gly Ser Leu Ser Arg Arg Ser Ser Leu Gly
                1845                    1850            (P) 1855
```

```
AGC CTT GAC CAG GTC CAG GGC TCC CAG GAA ACC CTT ATT CCT CCC AGG    5694
Ser Leu Asp Gln Val Gln Gly Ser Gln Glu Thr Leu Ile Pro Pro Arg
            1860                1865                1870

CCG TGA                                                            5700
Pro End

TGGCTGTGCA GTGTCCACAT GACCAAGGCG AGGGGGACAG TGCGTGCAGA AGCTCAGCCC  5760

TGCATGGCAG CCTCCCTCTG TCTCAGCCCT CCTGCTGAGC TGGGGCGGTC TGGAACCGAC  5820

CAGGAAGCCA GGAGCCTCCC CTGGCCAGCA AGAGGCATGA TTCTAAAGCA TCCAGAAAGG  5880

CCTGGTCAGT GCCACTCCCC AGCAGGACAT TAAAGTCTCT AGGTCTGTGG CAAAAAAAAA  5940

AAAAAAAAAA AAAAAAAAAA AAAAAAAAAA AAAAA                             5975
```

FIG. 9(a)-1

```
AGAAGGGAGG GCGAGCGTGG TGTGTGCGCG CTCGGGCGCC GGCGGCACCG CCGAGGTCTG    60

TTGGCAAAAG TCGCCCTTGA TGGCGGCGGA GGCGAGGCAG CCGCGGCGCC GAACAGCCGA   120

CGCGCGCTAG CGGGGTCCGC CCGCCCCTTT CCCAGAGCCC AGCGCCGCCG TTCGCCGCCG   180

CCGCCGCCCG CCCGCGCGCC GTTCGCCGCC GCCGCCGCCC GCGGGTGGCA GCGCCGCTCG   240

GTCCCCGGCC CCGGGGCCGG CTGGGGGGCG GTCGGGGCGT GTGAGGGGCT TGCTCCCAGC   300

TCGCGAAG                                                            308

ATG GCT GCG GGC CGC CCG CTG GCC TGG ACG CTG ACA CTT TGG CAG GCG     356
Met Ala Ala Gly Arg Pro Leu Ala Trp Thr Leu Thr Leu Trp Gln Ala
 1               5                  10                  15

TGG CTG ATC CTG ATC GGG CCC TCG TCG GAG GAG CCG TTC CCT TCA GCC     404
Trp Leu Ile Leu Ile Gly Pro Ser Ser Glu Glu Pro Phe Pro Ser Ala
            20                  25                  30

GTC ACT ATC AAG TCA TGG GTG GAT AAG ATG CAA GAA GAC CTG GTC ACA     452
Val Thr Ile Lys Ser Trp Val Asp Lys Met Gln Glu Asp Leu Val Thr
        35                  40                  45

CTG GCA AAA ACA GCA AGT GGA GTC CAT CAG CTT GTT GAT ATT TAT GAG     500
Leu Ala Lys Thr Ala Ser Gly Val His Gln Leu Val Asp Ile Tyr Glu
    50                  55                  60
```

AAA TAT CAA GAT TTG TAT ACT GTG GAA CCA AAT AAT GCA CGT CAG CTG 548
Lys Tyr Gln Asp Leu Tyr Thr Val Glu Pro Asn Asn Ala Arg Gln Leu
65 70 75 80

GTG GAA ATT GCA GCC AGA GAC ATT GAG AAG CTT CTC AGC AAC AGA TCT 596
Val Glu Ile Ala Ala Arg Asp Ile Glu Lys Leu Leu Ser Asn Arg Ser
85 90 • 95

AAA GCC CTG GTG CGC CTG GCT TTG GAA GCA GAG AAA GTT CAA GCA GCC 644
Lys Ala Leu Val Arg Leu Ala Leu Glu Ala Glu Lys Val Gln Ala Ala
100 105 110

CAC CAA TGG AGG GAA GAT TTT GCA AGC AAT GAA GTT GTC TAC TAT AAC 692
His Gln Trp Arg Glu Asp Phe Ala Ser Asn Glu Val Val Tyr Tyr Asn
115 120 125

GCG AAG GAT GAT CTT GAT CCT GAA AAA AAT GAC AGT GAA CCA GGC AGC 740
Ala Lys Asp Asp Leu Asp Pro Glu Lys Asn Asp Ser Glu Pro Gly Ser
130 135 • 140

CAG AGG ATC AAA CCT GTT TTC ATT GAC GAT GCT AAC TTT AGA AGA CAA 788
Gln Arg Ile Lys Pro Val Phe Ile Asp Asp Ala Asn Phe Arg Arg Gln
145 150 155 160

```
GTA TCC TAT CAG CAC GCA GCT GTC CAT ATC CCC ACT GAC ATC TAT GAA    836
Val Ser Tyr Gln His Ala Ala Val His Ile Pro Thr Asp Ile Tyr Glu
                165                 170                 175

GGA TCG ACA ATC GTG TTA AAC GAA CTC AAC TGG ACA AGT GCC TTA GAT    884
Gly Ser Thr Ile Val Leu Asn Glu Leu Asn Trp Thr Ser Ala Leu Asp
            180                 185  •              190

GAC GTT TTC AAA AAA AAT CGA GAG GAA GAC CCT TCA CTG TTG TGG CAG    932
Asp Val Phe Lys Lys Asn Arg Glu Glu Asp Pro Ser Leu Leu Trp Gln
        195                 200                 205

GTG TTT GGC AGT GCC ACT GGC CTG GCC CGG TAT TAC CCA GCT TCT CCA    980
Val Phe Gly Ser Ala Thr Gly Leu Ala Arg Tyr Tyr Pro Ala Ser Pro
    210                 215                 220

TGG GTT GAT AAT AGC CGA ACC CCA AAC AAG ATT GAT CTT TAT GAT GTA   1028
Trp Val Asp Asn Ser Arg Thr Pro Asn Lys Ile Asp Leu Tyr Asp Val
225                 230                 235                 240

CGC AGA AGA CCA TGG TAC ATC CAA GGT GCT GCA TCC CCT AAA GAT ATG   1076
Arg Arg Arg Pro Trp Tyr Ile Gln Gly Ala Ala Ser Pro Lys Asp Met
                245                 250                 255

CTT ATT CTG GTG GAT GTG AGT GGA AGC GTT AGT GGA CTG ACA CTC AAA   1124
Leu Ile Leu Val Asp Val Ser Gly Ser Val Ser Gly Leu Thr Leu Lys
            260                 265                 270
```

```
CTC ATC CGG ACA TCC GTC TCC GAA ATG TTG GAA ACC CTC TCA GAT GAT     1172
Leu Ile Arg Thr Ser Val Ser Glu Met Leu Glu Thr Leu Ser Asp Asp
        275                 280                 285

GAT TTT GTG AAC GTG GCT TCA TTT AAC AGC AAT GCT CAG GAT GTA AGC     1220
Asp Phe Val Asn Val Ala Ser Phe Asn Ser Asn Ala Gln Asp Val Ser
    290                 295                 300

TGC TTT CAG CAC CTT GTC CAA GCA AAT GTA AGA AAT AAG AAA GTG TTG     1268
Cys Phe Gln His Leu Val Gln Ala Asn Val Arg Asn Lys Lys Val Leu
305                 310                 315                 320

AAA GAT GCA GTG AAT AAT ATC ACA GCA AAA GGA ATC ACA GAT TAT AAG     1316
Lys Asp Ala Val Asn Asn Ile Thr Ala Lys Gly Ile Thr Asp Tyr Lys
                325  •              330                 335

AAG GGC TTT AGT TTT GCT TTT GAG CAG CTG CTT AAT TAT AAT GTA TCC     1364
Lys Gly Phe Ser Phe Ala Phe Glu Gln Leu Leu Asn Tyr Asn Val Ser
            340                 345                 350
                                                     •
AGA GCC AAC TGC AAT AAG ATT ATC ATG TTG TTC ACG GAC GGA GGA GAA     1412
Arg Ala Asn Cys Asn Lys Ile Ile Met Leu Phe Thr Asp Gly Gly Glu
        355                 360                 365
```

```
GAG AGA GCC CAG GAG ATA TTT GCC AAA TAC AAT AAA GAC AAG AAA GTA   1460
Glu Arg Ala Gln Glu Ile Phe Ala Lys Tyr Asn Lys Asp Lys Lys Val
    370                 375                 380

CGT GTA TTC ACA TTC TCA GTT GGC CAA CAT AAT TAC GAC AGA GGA CCT   1508
Arg Val Phe Thr Phe Ser Val Gly Gln His Asn Tyr Asp Arg Gly Pro
385                 390                 395                 400

ATT CAG TGG ATG GCT TGC GAA AAT AAA GGT TAT TAT TAT GAA ATT CCA   1556
Ile Gln Trp Met Ala Cys Glu Asn Lys Gly Tyr Tyr Tyr Glu Ile Pro
                405                 410                 415

TCC ATT GGA GCC ATA AGA ATT AAT ACT CAG GAA TAC CTA GAT GTT CTG   1604
Ser Ile Gly Ala Ile Arg Ile Asn Thr Gln Glu Tyr Leu Asp Val Leu
            420                 425                 430

GGA AGA CCG ATG GTT TTA GCA GGA GAC AAA GCT AAG CAA GTC CAA TGG   1652
Gly Arg Pro Met Val Leu Ala Gly Asp Lys Ala Lys Gln Val Gln Trp
        435                 440                 445

ACA AAT GTG TAC CTG GAT GCA CTG GAA CTG GGA CTT GTC ATT ACT GGA   1700
Thr Asn Val Tyr Leu Asp Ala Leu Glu Leu Gly Leu Val Ile Thr Gly
    450                 455                 460

ACT CTT CCG GTC TTC AAC ATA ACT GGC CAA TTT GAA AAT AAG ACA AAC   1748
Thr Leu Pro Val Phe Asn Ile Thr Gly Gln Phe Glu Asn Lys Thr Asn
465                 470                 475      .          480

TTA AAG AAC CAG CTG ATT CTT GGA GTG ATG GGA GTT GAT GTG TCT TTG   1796
Leu Lys Asn Gln Leu Ile Leu Gly Val Met Gly Val Asp Val Ser Leu
                485                 490                 495
```

```
GAA GAT ATT AAA AGA CTG ACA CCA CGT TTT ACA CTC TGC CCC AAT GGC     1844
Glu Asp Ile Lys Arg Leu Thr Pro Arg Phe Thr Leu Cys Pro Asn Gly
            500                 505                 510

TAC TAT TTT GCA ATT GAT CCT AAT GGT TAT GTG TTA TTA CAT CCA AAT     1892
Tyr Tyr Phe Ala Ile Asp Pro Asn Gly Tyr Val Leu Leu His Pro Asn
        515                 520                 525

CTT CAG CCA AAG CCT ATT GGT GTA GGT ATA CCA ACA ATT AAT TTG AGA     1940
Leu Gln Pro Lys Pro Ile Gly Val Gly Ile Pro Thr Ile Asn Leu Arg
    530                 535                 540

AAA AGG AGA CCC AAT GTT CAG AAC CCC AAA TCT CAG GAG CCA GTG ACA     1988
Lys Arg Arg Pro Asn Val Gln Asn Pro Lys Ser Gln Glu Pro Val Thr
545                 550                 555                 560

TTG GAT TTC CTC GAT GCA GAG TTG GAG AAT GAC ATT AAA GTG GAG ATT     2036
Leu Asp Phe Leu Asp Ala Glu Leu Glu Asn Asp Ile Lys Val Glu Ile
                565                 570                 575
```

```
CGA AAT AAA ATG ATC GAT GGA GAA AGT GGA GAA AAA ACA TTC AGA ACT    2084
Arg Asn Lys Met Ile Asp Gly Glu Ser Gly Glu Lys Thr Phe Arg Thr
            580                 585                 590

CTG GTT AAA TCT CAA GAT GAG AGA TAT ATT GAC AAA GGA AAC AGG ACA    2132
Leu Val Lys Ser Gln Asp Glu Arg Tyr Ile Asp Lys Gly Asn Arg Thr
        595                 600                 605  •

TAC ACG TGG ACT CCT GTC AAC GGC ACA GAT TAT AGC AGT TTG GCC TTG    2180
Tyr Thr Trp Thr Pro Val Asn Gly Thr Asp Tyr Ser Ser Leu Ala Leu
    610                 615                 620
                         •

GTA TTA CCA ACC TAC AGT TTT TAC TAT ATA AAA GCC AAA ATA GAA GAG    2228
Val Leu Pro Thr Tyr Ser Phe Tyr Tyr Ile Lys Ala Lys Ile Glu Glu
625                 630                 635                 640

ACA ATA ACT CAG GCC AGA TAT TCA GAA ACA CTG AAA CCG GAT AAT TTT    2276
Thr Ile Thr Gln Ala Arg Tyr Ser Glu Thr Leu Lys Pro Asp Asn Phe
                645                 650                 655

GAA GAA TCT GGC TAC ACA TTC CTA GCA CCA AGA GAT TAC TGC AGT GAC    2324
Glu Glu Ser Gly Tyr Thr Phe Leu Ala Pro Arg Asp Tyr Cys Ser Asp
            660                 665                 670

CTT AAA CCT TCA GAT AAT AAC ACT GAA TTT CTT TTA AAT TTC AAT GAG    2372
Leu Lys Pro Ser Asp Asn Asn Thr Glu Phe Leu Leu Asn Phe Asn Glu
        675          •      680                 685
```

```
TTT ATT GAT AGA AAA ACT CCA AAC AAC CCA TCC TGT AAT ACA GAC TTG      2420
Phe Ile Asp Arg Lys Thr Pro Asn Asn Pro Ser Cys Asn Thr Asp Leu
    690                 695      •          700

ATT AAT AGA GTC TTG CTG GAT GCA GGC TTT ACA AAT GAA CTT GTT CAA      2468
Ile Asn Arg Val Leu Leu Asp Ala Gly Phe Thr Asn Glu Leu Val Gln
705                 710                 715                 720

AAT TAC TGG AGT AAG CAG AAG AAT ATC AAG GGA GTG AAA GCA CGG TTT      2516
Asn Tyr Trp Ser Lys Gln Lys Asn Ile Lys Gly Val Lys Ala Arg Phe
                725                 730                 735

GTT GTG ACT GAT GGT GGG ATT ACC AGA GTT TAT CCC AAA GAG GCT GGA      2564
Val Val Thr Asp Gly Gly Ile Thr Arg Val Tyr Pro Lys Glu Ala Gly
            740                 745                 750

GAA AAT TGG CAG GAA AAC CCA GAG ACA TAT GAA GAC AGC TTC TAT AAA      2612
Glu Asn Trp Gln Glu Asn Pro Glu Thr Tyr Glu Asp Ser Phe Tyr Lys
        755                 760                 765

AGG AGC CTC GAT AAT GAT AAC TAC GTT TTC ACT GCT CCC TAC TTT AAC      2660
Arg Ser Leu Asp Asn Asp Asn Tyr Val Phe Thr Ala Pro Tyr Phe Asn
    770                 775                 780                  •
```

| | | | | | | | | | | | | | | | | |
|---|---|---|---|---|---|---|---|---|---|---|---|---|---|---|---|---|
| AAA | AGT | GGA | CCT | GGG | GCC | TAT | GAG | TCA | GGC | ATT | ATG | GTA | AGC | AAA | GCT | 2708 |
| Lys | Ser | Gly | Pro | Gly | Ala | Tyr | Glu | Ser | Gly | Ile | Met | Val | Ser | Lys | Ala | |
| 785 | | | | | 790 | | | | | 795 | | | | | 800 | |
| GTA | GAA | ATA | TAT | ATC | CAA | GGA | AAA | CTT | CTT | AAA | CCT | GCA | GTT | GTT | GGA | 2756 |
| Val | Glu | Ile | Tyr | Ile | Gln | Gly | Lys | Leu | Leu | Lys | Pro | Ala | Val | Val | Gly | |
| | | | | 805 | | | | | 810 | | | | | 815 | | |
| ATT | AAA | ATT | GAT | GTA | AAT | TCT | TGG | ATA | GAG | AAT | TTC | ACC | AAA | ACT | TCA | 2804 |
| Ile | Lys | Ile | Asp | Val | Asn | Ser | Trp | Ile | Glu | Asn | Phe | Thr | Lys | Thr | Ser | |
| | | | 820 | | | | | 825 | | | | | 830 | | | |
| ATC | AGG | GAT | CCG | TGT | GCT | GGT | CCA | GTT | TGT | GAC | TGC | AAA | CGA | AAC | AGT | 2852 |
| Ile | Arg | Asp | Pro | Cys | Ala | Gly | Pro | Val | Cys | Asp | Cys | Lys | Arg | Asn | Ser | |
| | | 835 | | | | | 840 | | | | | 845 | | | (P) | |
| GAT | GTA | ATG | GAT | TGT | GTG | ATT | CTA | GAT | GAC | GGT | GGG | TTT | CTT | TTG | ATG | 2900 |
| Asp | Val | Met | Asp | Cys | Val | Ile | Leu | Asp | Asp | Gly | Gly | Phe | Leu | Leu | Met | |
| | 850 | | | | | 855 | | | | | 860 | | | | | |
| GCC | AAC | CAT | GAT | GAT | TAT | ACC | AAT | CAG | ATT | GGA | AGA | TTC | TTT | GGA | GAG | 2948 |
| Ala | Asn | His | Asp | Asp | Tyr | Thr | Asn | Gln | Ile | Gly | Arg | Phe | Phe | Gly | Glu | |
| 865 | | | | | 870 | | | | | 875 | | | | | 880 | |
| ATT | GAT | CCA | AGC | TTG | ATG | AGA | CAC | CTG | GTC | AAT | ATA | TCA | GTT | TAT | GCC | 2996 |
| Ile | Asp | Pro | Ser | Leu | Met | Arg | His | Leu | Val | Asn | Ile | Ser | Val | Tyr | Ala | |
| | | | | 885 | | | | | 890 | • | | | | 895 | | |

```
TTT AAC AAA TCT TAT GAT TAT CAG TCG GTG TGT GAA CCT GGT GCT GCG     3044
Phe Asn Lys Ser Tyr Asp Tyr Gln Ser Val Cys Glu Pro Gly Ala Ala
     •      900                 905                 910

CCA AAG CAG GGA GCA GGG CAC CGC TCG GCT TAT GTG CCA TCA ATA GCA     3092
Pro Lys Gln Gly Ala Gly His Arg Ser Ala Tyr Val Pro Ser Ile Ala
        915                 920                 925

GAC ATA CTG CAG ATT GGA TGG TGG GCC ACT GCT GCT GCC TGG TCT ATT     3140
Asp Ile Leu Gln Ile Gly Trp Trp Ala Thr Ala Ala Ala Trp Ser Ile
     930                 935                 940

CTT CAG CAG TTT CTG TTG AGT TTG ACT TTT CCA CGG CTC CTT GAG GCA     3188
Leu Gln Gln Phe Leu Leu Ser Leu Thr Phe Pro Arg Leu Leu Glu Ala
945                 950                 955                 960

GCT GAT ATG GAG GAT GAC GAC TTC ACT GCC TCC ATG TCA AAG CAG AGC     3236
Ala Asp Met Glu Asp Asp Asp Phe Thr Ala Ser Met Ser Lys Gln Ser
                965                 970                 975

TGC ATC ACT GAG CAA ACC CAG TAT TTC TTC GAT AAT GAC AGC AAA TCG     3284
Cys Ile Thr Glu Gln Thr Gln Tyr Phe Phe Asp Asn Asp Ser Lys Ser
            980                 985          •      990
```

TTC AGT GGG GTA TTA GAC TGT GGG AAT TGT TCC AGA ATC TTT CAT GTA 3332
Phe Ser Gly Val Leu Asp Cys Gly Asn Cys Ser Arg Ile Phe His Val
995 1000 • 1005

GAA AAG CTC ATG AAC ACC AAT TTA ATA TTC ATA ATG GTA GAG AGC AAG 3380
Glu Lys Leu Met Asn Thr Asn Leu Ile Phe Ile Met Val Glu Ser Lys
1010 1015 1020

GGG ACA TGT CCC TGT GAC ACA CGG CTG CTC ATA CAA GCA GAG CAA ACT 3428
Gly Thr Cys Pro Cys Asp Thr Arg Leu Leu Ile Gln Ala Glu Gln Thr
1025 1030 1035 1040

TCT GAT GGA CCA GAT CCT TGT GAT ATG GTT AAG CAA CCC AGA TAT CGA 3476
Ser Asp Gly Pro Asp Pro Cys Asp Met Val Lys Gln Pro Arg Tyr Arg
1045 1050 1055

```
AAA GGG CCA GAT GTC TGC TTT GAC AAC AAT GTC CTG GAG GAT TAT ACT    3524
Lys Gly Pro Asp Val Cys Phe Asp Asn Asn Val Leu Glu Asp Tyr Thr
            1060                1065  •             1070

GAC TGC GGT GGG GTC TCT GGA TTA AAT CCT TCC CTG TGG TCC ATC ATC    3572
Asp Cys Gly Gly Val Ser Gly Leu Asn Pro Ser Leu Trp Ser Ile Ile
        1075                1080  •             1085

GGG ATA CAG TTT GTA CTG CTT TGG CTG GTT TCT GGC AGC AGA CAC TGC    3620
Gly Ile Gln Phe Val Leu Leu Trp Leu Val Ser Gly Ser Arg His Cys
    1090                1095                1100

CTG TTA TGA                                                        3629
Leu Leu End
1105

CCTTCTAAAA CCAAATCTCC ATAATTAAAC TCCAGACCCT GCCACAACAT GATCCCTCCG  3689

TTATGTTAAA GTAGGGTCAA CTGTTAAATC AGAACATTAG CTGGGCCTCT GCCATGGCAG  3749

AGCCCTAAGG CGCAGACTCA TCAGGCACCC ACTGGCTGCA TGTCAGGGTG TCC         3802
```

FIG. 9(f)-2

CALCIUM CHANNEL COMPOSITIONS AND METHODS

The work was supported in part by the Government under Grants HL-37187, HL-14388 and HL-39265 awarded by the National Institutes of Health (DHHS). The Government may have certain rights in the invention.

TECHNICAL FIELD

BACKGROUND OF THE INVENTION

Calcium channels are membrane-spanning, multisubunit proteins that allow controlled entry of $Ca^{+2}$ ions into cells from the extracellular fluid. All cells throughout the animal kingdom, and at least some bacterial, fungal and plant cells, possess one or more types of calcium channel.

The most common type of calcium channel is voltage-dependent. In a voltage-dependent channel, the "opening" which allows there to begin an influx of $Ca^{+2}$ ions into the cells requires a depolarization to a certain level of the potential difference between the inside of the cell bearing the channel and the extracellular medium bathing the cell. The rate of influx of $Ca^{+2}$ into the cell depends on this potential difference. All "excitable" cells in animals, such as neurons of the central nervous systems, peripheral nerve cells, and muscle cells, including those of skeletal muscles, cardiac muscles, and venous and arterial smooth muscles, have voltage-dependent calcium channels.

Calcium channels are physiologically important because the channels have a central role in regulating intracellular $Ca^{+2}$ levels, which levels are important for cell viability and function. Thus, intracellular $Ca^{+2}$ concentrations are implicated in a number of vital processes in animals, such as neurotransmitter release, muscle contraction, pacemaker activity, and secretion of hormones and other substances.

A number of compounds useful in treating various diseases in animals, including humans, are thought to exert their beneficial effects by modulating functions of voltage-dependent calcium channels. Many of these compounds bind to calcium channels and block, or reduce the rate of, influx of $Ca^{+2}$ into cells in response to depolarization of the inside and outside of the cells.

An understanding of the pharmacology of compounds that interact with calcium channels, and the ability to rationally design compounds that will interact with calcium channels to have desired therapeutic effects, have been hampered by a lack of understanding of the structure of channel subunits and the genes that code for them. Thus, it has not been possible to obtain the large amounts of highly purified channel subunits that are required to understand, at the molecular level, the nature of the subunits and their interactions with one another, with the cell membranes across which the channels allow $Ca^{+2}$ ions to pass, with $Ca^{+2}$ and other ions, and with low molecular weight compounds that affect channel function. For example, with the availability of large amounts of purified calcium channel subunits, functional channels could be prepared and used to screen the effects of compounds on channel function, thereby providing a basis for the design of therapeutic agents which affect the calcium channel, or various combinations of channel subunits could be crystallized and have their structures determined to high resolution employing X-ray or neutron diffraction techniques, providing yet another basis for rational design of therapeutic agents that affect channel function.

Certain diseases, such as Lambert-Eaton Syndrome, involve autoimmune interactions with calcium channels. The ready availability of each of the calcium channel subunits would make possible immunoassays for the diagnosis of such diseases and an understanding of them at the molecular level that could lead to effective methods of treatment.

The lack of information on genes that code for calcium channel subunits has prevented the understanding of the molecular properties of the mature calcium channel subunits and their precursor proteins (i.e., the mature subunits with signal peptides appended to the amino-terminus) and the regulation of expression of calcium channel subunits. An understanding of these properties, and of how expression of calcium channel subunit genes is regulated, may provide the basis for designing therapeutic agents which have beneficial effects through affecting calcium channel function or concentration. Furthermore, the availability of sequences of genes coding for calcium channel subunits would make possible the diagnosis of defects in genes coding for such subunits, which might underlie a number of diseases.

The availability of a DNA with the sequence of a segment of at least about 14 and more preferably at least about 30 nucleotides of a cDNA encoding a subunit of a calcium channel from the cells of a tissue of an animal would make possible the isolation and cloning of cDNAs, and possibly genomic DNAs, coding for the corresponding subunit of different calcium channels from the same or different tissues and animals of the same or different species. The availability of the sequences of numerous full-length cDNAs coding for corresponding subunits of calcium channels from a variety of tissues and animal species would contribute to elucidating structure-function relationships in the subunits. This knowledge, in turn, would be useful in the design of therapeutic agents whose activities are exerted through binding to calcium channels.

In skeletal muscle, where voltage-dependent calcium channels have been best characterized, voltage-dependent calcium channels are thought to consist of two large subunits, of between about 130 and about 200 kilodaltons ("kD") in molecular weight, and a number (generally thought to be two or three) of different smaller subunits, of less than about 60 kD in molecular weight. At least one of the larger subunits and possibly some of the smaller are glycosylated. Some of the subunits are capable of being phosphorylated. There has been confusion in the art concerning the naming of the various subunits of voltage-dependent calcium channels.

The two large subunits of voltage-dependent calcium channels are designated herein the "$\alpha_1$-subunit" and the "$\alpha_2$-subunit".

The $\alpha_1$-subunit is not detectably changed in molecular weight when treated with dithiothreitol ("DTT") or with enzymes which catalyze removal of N-linked sugar groups from glycosylated proteins. The $\alpha_1$-subunit has a molecular weight of about 150 to about 170 kD when analyzed by sodium dodecylsulfate ("SDS")-polyacrylamide gel electrophoresis ("PAGE") after isolation from mammalian muscle tissue and has specific binding sites for various 1,4-dihydropyridines ("DHPs") and phenylalkylamines.

The $\alpha_2$-subunit is somewhat less well characterized than the $\alpha_1$-subunit, although recent work by Ellis et al. (see PCT Application No. WO 89/09834 and *Science,* 241, 1661–1664 (1988)), has provided a great deal of additional information concerning this subunit. The molecular weight of the $\alpha_2$-subunit is at least about 130–150 kD, as determined by SDS-PAGE analysis in the presence of DTT after isolation from mammalian muscle tissue. However, in SDS-PAGE under non-reducing conditions (in the presence of N-ethylmaleimide), the $\alpha_2$-subunit migrates with a band of about 160–190 kD. It is presently believed that the smaller fragment (of about 30 kD), which appears to be released upon reduction of the $\alpha_2$-subunit, is the carboxy terminus of the primary translation product of the $\alpha_2$-subunit mRNA. Regardless, however, of whether the two fragments are different subunits of the calcium channel or whether both fragments are products of the same gene (and, consequently, the $\alpha_2$-subunit is about 160–190 kD and is split into (at least) two fragments upon reduction), there is evidence that the $\alpha_2$-subunit, whatever its size, and the corresponding fragment produced under reducing conditions, whether part of the $\alpha_2$-subunit or not, are glycosylated with at least N-linked sugars. In addition there is evidence that the $\alpha$2-subunit and the corresponding fragment produced under reducing conditions do not have specified binding sites for 1,4-dihydropyridines and phenylalkylamines, which species are known to bind to the $\alpha_1$-subunit.

The $\beta$-subunit of the calcium channel has only recently been characterized as having an apparent molecular mass of 52–65 kD (as determined by SDS-PAGE analysis). It is comprised of consensus phosphorylation sites and has been shown by biochemical methods to be phosphorylated. This subunit is insensitive to reducing conditions.

The $\gamma$-subunit of the calcium channel has not been observed in all purified preparations, depending on the source of material analyzed, the investigating laboratory, and so on. Because of its irregular appearance in the hands of some investigators, this particular subunit also remains relatively poorly characterized. The native material appears to be a glycoprotein with an apparent molecular mass of 30–33 kD, as determined by SDS-PAGE analysis. The native protein is believed to be glycosylated since its apparent molecular mass decreases after digestion with neuraminidase followed by endoglycosidase F.

Reference herein to the precursor of an $\alpha_1$-subunit means the protein with the amino acid sequence corresponding to the sequence of the full-length mRNA which, upon translation, results, ultimately, in $\alpha_1$-subunit resident as part of a calcium channel in a cell membrane. The precursor protein is converted by various, not presently well understood, processing steps to produce the $\alpha_1$-subunit.

Similarly, reference herein to the precursor of an $\alpha_2$-subunit means the protein with the amino acid sequence corresponding to the sequence of the full-length mRNA which, upon translation, results, ultimately, in $\alpha_2$-subunit resident as part of a calcium channel in a cell membrane. The precursor protein is converted by various processing steps into the $\alpha_2$-subunit. As with the $\alpha_1$-subunit, the details of the processing between the precursor and the mature $\alpha_2$-subunit are not clear, but the processing presumably involves at least removal of a leader sequence (i.e., a signal peptide), glycosylation, and cleavage to yield what is now thought to be $\delta$-subunit of the calcium channel.

Similarly, reference herein to the precursor of a $\beta$-subunit means the protein with the amino acid sequence corresponding to the sequence of the full-length mRNA which, upon translation, results ultimately, in $\beta$-subunit resident as part of a calcium channel in a cell membrane. The precursor protein is converted by various, not presently well understood, processing steps into the $\beta$-subunit.

Similarly, reference herein to the precursor of a $\gamma$-subunit means the protein with the amino acid sequence corresponding to the sequence of the full-length mRNA which, upon translation, results ultimately, in $\gamma$-subunit resident as part of a calcium channel in a cell membrane. The precursor protein is converted by various, not presently well understood, processing steps into the $\gamma$-subunit.

The cDNA and corresponding amino acid sequence of the $\alpha_1$-subunit precursor of a rabbit back skeletal muscle calcium channel has been reported. See Tanabe et al., *Nature* 328, 313–318 (1987).

The cDNA and corresponding amino acid sequences of the $\alpha_2$-subunit precursor of a rabbit back skeletal muscle calcium channel and a human neuronal calcium channel have also been reported. See Ellis, et al., PCT Application No. WO 89/09834 (1989) and *Science* 241, 1661–1664 (1988).

The cDNA and corresponding amino acid sequence of the $\beta$-subunit precursor of a rabbit back skeletal muscle calcium channel has also been reported. See Ruth et al., *Science* 245, 1115–1118 (1989).

Up to now, however, the cDNA and corresponding amino acid sequence of the $\gamma$-subunit precursor of a calcium channel have not been reported in the literature.

Calcium channel activity, measured electrophysiologically by voltage-clamp techniques, has been induced in Xenopus laevis oocytes when total mRNA isolated from mammalian brain or cardiac muscle is injected into the oocytes. Also, it has been reported that calcium channel-containing preparations, when reconstituted into lipid bilayers, confer voltage-dependent calcium channel activity on the bilayers.

However, there is no evidence that any one of the calcium channel subunits alone provides a natively functional calcium channel in oocytes, lipid bilayers or any other situation. It has been recently reported by Hofmann, et al., Trends in Pharmacology. Sci. 8, 393–398 (1987) that mRNA prepared using the cDNA of $\alpha_1$-subunit obtained by Tanabe, et al. was unable to induce calcium channel activity in Xenopus laevis oocytes.

SUMMARY OF THE INVENTION

In accordance with the present invention, there is provided the cDNA and corresponding amino acid sequence of the $\gamma$-subunit precursor of a calcium channel.

There are now available well-characterized cDNA clones encoding each of the four calcium channel subunits, thus enabling one to incorporate various combinations of such cDNAs into recombinant expression systems. In this way, one can assess the contribution of the various calcium channel subunits to the transport and regulation of calcium ions.

BRIEF DESCRIPTION OF THE FIGURES

FIG. 1 provides the cDNA nucleotide sequence and the amino acid sequence for the γ-subunit of a calcium channel.

FIG. 4 provides the amino acid sequence for, and a nucleotide sequence encoding the β-subunit of a calcium channel.

FIG. 8 provides the amino acid sequence for, and a nucleotide sequence encoding the $\alpha_1$-subunit of a calcium channel.

FIG. 9 provides the amino acid sequence for, and a nucleotide sequence encoding the $\alpha_2$-subunit of a calcium channel.

DETAILED DESCRIPTION OF THE INVENTION

Figure 2:
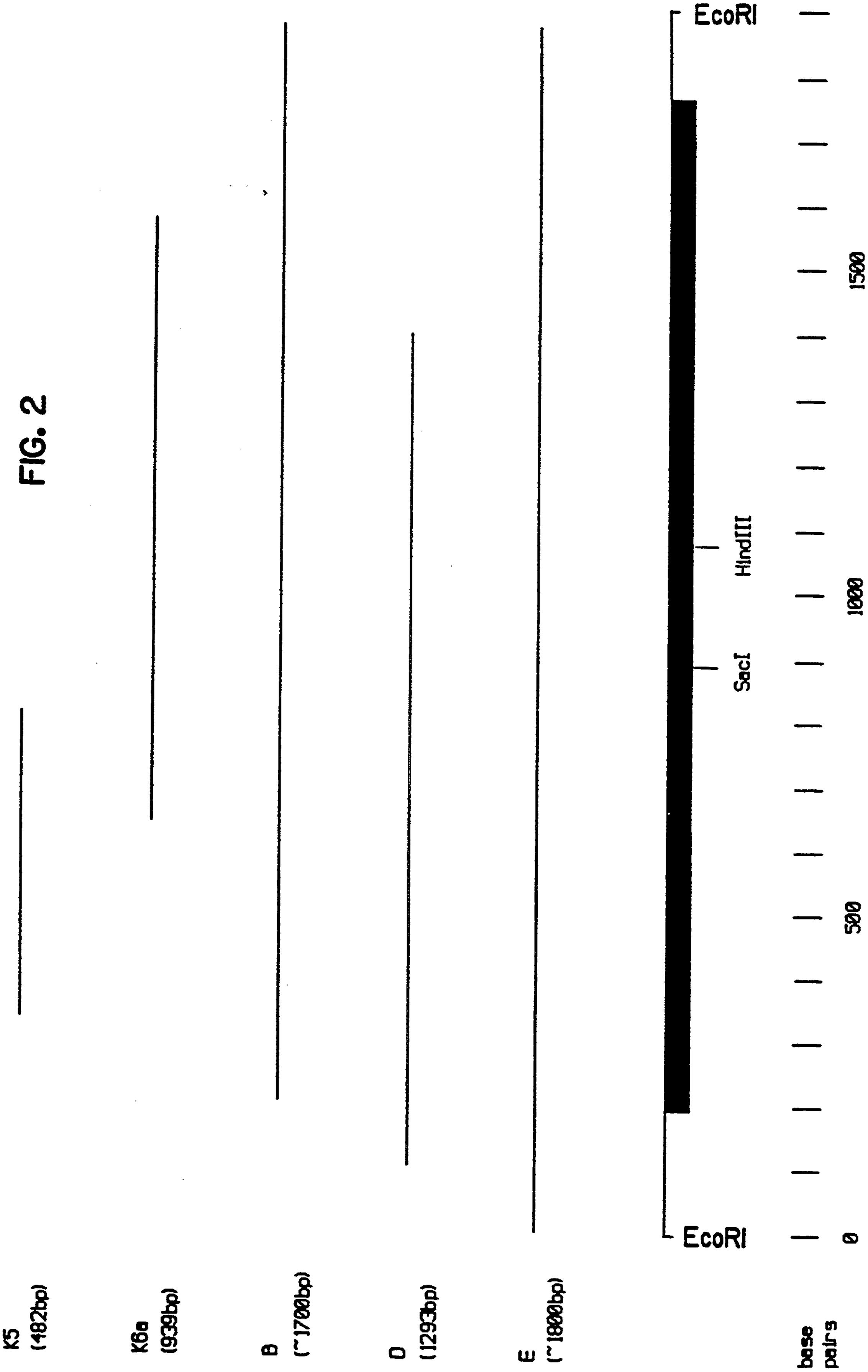
FIG. 2 is a restriction map of a cDNA sequence which encodes the β-subunit of a calcium channel, and shows the orientation of various cDNAs encoding the β-subunit sequence.

In accordance with the present invention, we have discovered a cDNA which codes for the γ-subunit of an animal calcium channel (see FIG. 1).

Thus in one of its aspects, the invention is a DNA fragment which comprises a cDNA which codes for the γ-subunit of an animal calcium channel, and the RNA, coding for such a subunit, made upon transcription of such a DNA according to the invention.

In another of its aspects, the invention is a substantially pure γ-subunit of an animal calcium channel.

By a "substantially pure" subunit or protein is meant a subunit or protein that is sufficiently free of other polypeptide contaminants to be considered homogeneous by SDS-PAGE or to be unambiguously sequenced.

In another of its aspects, the invention entails an eukaryotic cell with an heterologous calcium channel, said cell made by a process comprising administering to said cell a first composition, which consists essentially of a first RNA or cDNA which is translatable in said cell into the precursor of the γ-subunit of a calcium channel of an animal of a first species, and at least one of a second composition selected from the group consisting essentially of a second RNA or cDNA which is translatable in said cell into the precursor of the $\alpha_1$-subunit of a calcium channel of an animal of a second species, a third RNA or cDNA which is translatable in said cell into the precursor of the $\alpha_2$-subunit of a calcium channel of an animal of a third species, and a fourth RNA or cDNA which is translatable in said cell into the precursor of the β-subunit of a calcium channel of an animal of a fourth species, wherein said first, second, third and fourth species can be the same or different. Preferred cells for this purpose are *Xenopus laevis* oocytes.

In yet another of its aspects, the present invention entails a method for preparing an heterologous calcium channel by expressing the RNA or cDNA administered to the above-described eukaryotic cells.

In another of its aspects, the invention entails a method for assaying a compound for calcium channel agonist or antagonist activity which comprises electrophysiologically measuring the calcium channel activity of an RNA- or cDNA-containing eukaryotic cell prepared as described above when such cell is exposed to a solution of the compound being tested for such activity. For similar methods applied with *Xenopus laevis* oocytes and acetylcholine receptors, see e.g., Mishina et al. Nature 313, 364 (1985) and, with such oocytes and sodium channels, see Noda et al., Nature 322, 826–828 (1986).

In a further of its aspects, the invention is an eukaryotic cell containing a DNA which comprises a cDNA which can be expressed to make the γ-subunit of a calcium channel. Such a cell according to the invention can also contain at least one of the following additional DNA fragments selected from the group consisting essentially of:

- a second cDNA which codes for the precursor of the $\alpha_1$-subunit of a calcium channel of an animal of a second species,
- a third cDNA which codes for the precursor of the $\alpha_2$-subunit of a calcium channel of an animal of a third species, and
- a fourth cDNA which codes for the precursor of the β-subunit of a calcium channel of an animal of a fourth species, wherein said first, second, third and fourth species can be the same or different. Preferably, the $\alpha_1$-subunit, the $\alpha_2$-subunit, the β-subunit or the γ-subunit made from such cDNA in such a cell will be foreign to the cell, i.e., will have an amino acid sequence which differs from that of any calcium channel $\alpha_1$-subunit, $\alpha_2$-subunit, β-subunit or γ-subunit which occurs in a cell of the same type which does not contain a DNA from which the $\alpha_1$-subunit, the $\alpha_2$-subunit, the β-subunit or the γ-subunit encoded by such a cDNA is expressed. Preferred among such cells are those of mammalian origin, such as COS cells, NIH3T3 cells, mouse L cells or the like, or those of yeast such as *S. cerevisiae, P. pastoris*, or *C. tropicalis*. Methods of making such cells of the invention, i.e., by transforming cells with suitable heterologous DNAs, to be maintained in the cell as episomes or integrated into chromosomal DNA of the cell, and then culturing transformants or subculturing (or passaging, in the case of mammalian cells) from such a culture or a subculture thereof, are well known to those of ordinary skill in the art.

In yet another aspect of the present invention, there is provided a method for the production of the γ-subunit of a calcium channel, comprising expressing the cDNAs contained in the eukaryotic cells as described above.

Among such cDNA-containing cells of the invention, the invention entails also an eukaryotic cell with an heterologous calcium channel, said calcium channel made by a process comprising expression of a first cDNA, which codes for the precursor of the γ-subunit of a calcium channel of an animal of a first species, and at least one of the following additional DNA fragments selected from the group consisting essentially of:

a second cDNA which codes for the precursor of the $\alpha_1$-subunit of a calcium channel of an animal of a second species, a third cDNA which codes for the precursor of the $\alpha_2$-subunit of a calcium channel of an animal of a third species, and a fourth cDNA which codes for the precursor of the $\beta$-subunit of a calcium channel of an animal of a fourth species, wherein said first, second, third and fourth species can be the same or different. Usually at least one of said precursors of said $\alpha_1$-subunit, $\alpha_2$-subunit, $\beta$-subunit and $\gamma$-subunit is foreign to said cell. Again, preferred among such cells are those of mammalian origin or those of yeast such as *S. cerevisiae, P. pastoris* or C. *tropicalis.* In a preferred embodiment, such a cell will also contain another heterologous gene, which comprises a transcriptional control element (e.g., a promoter or promoter/enhancer combination), which is active in said cell and the transcriptional activity of which responds, either directly or indirectly, to an ion or molecule capable of entering said cell through a functional calcium channel (e.g., $Ca^{++}$, $Ba^{++}$, $Ca^{++}$ionophores), linked operatively for expression to a structural gene for an indicator protein, such as chloramphenicol acetyltransferase, luciferase or $\beta$-galactosidase.

In a further aspect of the present invention, there is provided a method to identify compounds which are agonists or antagonists of mammalian calcium channels whereby an eukaryotic cell with an heterologous calcium channel, prepared as described above, is contacted with the compound to be tested, and the effect of the compound to be tested on the calcium concentration in the cell is then measured, either directly or indirectly.

These cells of the invention, which have functional, foreign calcium channels (i.e., functional calcium channels wherein at least one of the calcium channel subunits is not native to the cell) will be useful for, among other purposes, assaying a compound for calcium channel agonist or antagonist activity. First, such a cell can be employed to measure the affinity of such a compound for the functional calcium channel. Secondly, such a cell can be employed to measure electrophysiologically the calcium channel activity in the presence of the compound being tested as well as an ion or molecule, such as $Ca^{++}$or $Ba^{++}$, which is known to be capable of entering the cell through the functional channel. For similar studies which have been carried out with the acetylcholine receptor, see Claudio et al. Science 238 1688–1694 (1987). These methods for assaying a compound for calcium channel agonist or antagonist activity are also part of the present invention.

In a still further embodiment of the present invention, there is provided a method for the production of functional, foreign calcium channels by expressing the cDNA-containing cells as described above.

Such cells according to the invention, in the preferred embodiment, wherein the cell also contains an heterologous gene with a transcriptional control element, which is active in the cell and responsive, either directly or indirectly, to an ion or molecule capable of entering the cell through a functional calcium channel and is linked operatively for expression to a structural gene for an indicator protein, can also be employed, in another method according to the invention for assaying a compound for calcium channel agonist or antagonist activity. This method comprises exposing a culture of such cells to a solution of a compound being tested for such activity, together with an ion or molecule which is capable of entering the cells through a functional calcium channel and affecting, either directly or indirectly, the activity of the transcriptional control element controlling transcription of the gene for the indicator protein, and comparing the level of expression, in the cells of the culture, of the gene for the indicator protein with the level of such expression in the cells of another, control culture of such cells.

A "control culture," as clearly understood by those of skill in the art, will be a culture that is, and is treated, substantially the same as the culture exposed to the compound being assayed, except that the control culture is not exposed to the compound being assayed. Alternatively, a control culture will be a culture that is exposed to the compound being assayed, but has not been transformed with calcium channel subunit encoding sequences, but is otherwise treated substantially the same as the test culture. Levels of expression of the genes for the indicator proteins are ascertained readily by the skilled by known methods, which involve measurements of the concentration of indicator protein via assays for detectable compounds produced in reactions catalyzed by the indicator protein.

As indicated above, indicator proteins are enzymes which are active in the cells of the invention and catalyze production of readily detectable compounds, e.g., chromogens, fluorescent compounds, radioactively labeled compounds, and the like.

The invention entails also a labeled (e.g., $^{32}P$ or a biotinylated) RNA or single-stranded DNA of at least 14 (preferably at least 30) bases in length in a sequence which comprises a sequence of at least 14 (preferably at least 30) contiguous bases between bases 1 and 1171, inclusive, in FIG. 1, which encodes rabbit skeletal muscle $\gamma$-subunit. The use of such DNAs and RNAs as probes, to identify and isolate cDNAs coding calcium channel $\gamma$-subunits or to identify tissue in which $\gamma$-subunit mRNA is made, is clear to those skilled in the art. In this regard, see, e.g., Example 4.

The primary strategy for cloning cDNAs encoding the $\gamma$ polypeptide subunit of the DHP-sensitive calcium channel from rabbit skeletal muscle was to screen rabbit back skeletal muscle cDNA expression libraries with an antibody probe specific to the protein. See generally Ausubel et al., *Current Protocols in Molecular Biology*, Wiley-Interscience, New York (1987); Davis et al., *Basic Methods in Molecular Biology*, Elsevier Science Publishing Co., New York (1986) .

Polyclonal antisera for the $\gamma$ polypeptide subunit was prepared in guinea pigs as described by Sharp and Campbell, *J. Biol. Chem.* 264, 2816–2825 (1989). The $\gamma$-specific polyclonal antisera were used for screening of approximately $1.0\times10^6$ plaques of recombinant phages of a random-primed lambda gt11 cDNA library.

In an initial screen with the guinea pig $\gamma$-specific polyclonal antisera, two cDNA clones were isolated and identified as J6 and J10. These clones were shown to be related to each other by partial sequencing and restriction digestion analysis. These cDNAs were used to screen an oligo dT-primed lambda gt11 cDNA library to isolate overlapping cDNA clones. Three clones were isolated from this screen, and were identified as G2, G10 and G11. One of these clones (G10) was partially sequenced. The insert from clone G10 was then oriented with respect to the inserts from clones J6 and J10. The cDNA insert from clone J10 was then used to screen pooled recombinants from a rabbit skeletal muscle cDNA library [MacLennan et al, *Nature* 316., 696 (1985)] constructed according to Okayama and Berg [*Mol. Cell Biol.* 3, 280–289 (1983)]. Of the positive clones identified from this screening, clone G4-3 was found to encompass and extend the cDNA inserts in clones J6, J10 and G10.

The cDNA clones were then analyzed to establish the coding DNA sequence of the γ-subunit of the calcium channel. Approximately 1171 nucleotides of γ-subunit cDNA was cloned, which is consistent with an estimated 1200 nucleotide γ-subunit mRNA.

FIG. 1 represents the 1,171 nucleotides of the cDNA sequence encoding the γ-subunit and its precursor, including 48 nucleotides of 5′ untranslated sequence, a 666 nucleotide open reading frame, and 457 nucleotides of 3′ untranslated sequence.

The 1171-nucleotide cDNA sequence set forth in FIG. 1 contains a 666-nt open reading frame coding for 222 amino acids. The deduced amino acid sequence yields a calculated molecular weight of 25,058 Dalton, which is in approximate agreement to the observed molecular mass of 32 kD for the glycosylated (1–3) and 20 kD for the chemically de-glycosylated forms of the γ-subunit, as determined by SDS-polyacrylamide gel electrophoresis. The deduced amino acid sequence is also in agreement with the authentic $NH_2$-terminus of the γ-subunit as determined by protein sequence analysis on the purified skeletal muscle protein (see Example 5).

The present invention makes available well-characterized cDNA clones encoding each of the four subunits of the rabbit skeletal muscle DHP-sensitive $Ca^{2+}$ channel. It is, therefore, now possible to incorporate various combinations of these cDNAs into recombinant DNA expression systems to make functional calcium channels and to assess the relative contribution of each subunit to the formation of functional $Ca^{2+}$ channels.

The present invention will now be described in greater detail by reference to the following non-limiting examples.

EXAMPLE 1

Preparation of β and γ Antibody Probes

The DHP receptor was extracted from heavy microsomes and triads of rabbit skeletal muscle, and then purified, following the procedures described in Sharp, et al. (1987), *J. Biol. Chem.* 262, 12309–12315. Individual components of the receptor were separated by SDS-PAGE on a 5–16% acrylamide gradient gel in the absence (nonreducing condition) or presence (reducing condition) of 1% 2-mercaptoethanol in the sample buffer. The gels were stained for 5–10 min with Coomassie Blue stain in 10% acetic acid, 25% isopropanol, and then destained in distilled water. Individual bands were visualized. The complex contains at least four subunits: α1 (170,000 Da), α2 (175,000 Da nonreduced/150,000 Da reduced), β (52,000 Da) and γ (32,000 Da), which appear to be present roughly in a 1:1:1:1 stoichiometric ratio. The purified complex or individual subunits present in sliced gel bands were then used to immunize experimental animals to induce the production of polyclonal antibodies as described below.

A. β-enriched Antiserum

One sheep, identified as Anti-DHPR#1, was immunized subcutaneously with 500 μg of the purified DHPR protein (not gel separated) in Freund's Complete Adjuvant. Eight weeks post immunization, a subcutaneous boost of 500 μg purified DHPR protein in Freund's Complete Adjuvant was given. A serum sample was collected one week later. A second boost, identical to the first, was given one month after the first bleed, and a second bleed was performed one week after the second boost.

Aliquots of the two bleeds, and aliquots of a preimmunized serum sample, were characterized for titer and reactivity to the DHPR subunit proteins. Two to five μg of DHPR subunit proteins purified as described above were applied to nitrocellulose, and reacted with 10-fold serial dilutions of the three serum samples. Primary antibody was detected using a peroxidase-labeled secondary antibody and 1-chloro-4-naphthol as a development substrate. The aliquot of serum from the second bleed demonstrated the highest titer of β-specific antisera (>1:1000), and was used in the affinity purification procedure.

B. γ-specific Antiserum

The γ polyclonal serum was prepared in guinea pigs as previously described [Sharp and Campbell, (1989), *J. Biol. Chem.* 264, 2816–2825]. Briefly, guinea pig #16 was immunized at the intervals described in Sharp and Campbell ibid. with a single, homogenized 5 mm×15 mm gel band corresponding to the 32 KD γ subunit (γ content of the gel band was approximately 2 μg). The collected ascites was characterized by Immunoblot analysis as described in (A), above. Samples with titers >1:1000 for the γ subunit were used for further analysis.

C. Affinity Purification

Antibodies raised against the β and γ subunit proteins were affinity purified from serum of injected sheep and guinea pigs, respectively, following the protocol of Sharp and Campbell (1989), *J. Biol. Chem.* 264, 2816–2825, using Immobilon strips. In brief, 200 μg of purified rabbit dihydropyridine receptor were separated by preparative SDS-PAGE and electrophoretically transferred to Immobilon-P membranes (Millipore; resolving gel size=12.5 cm×13 cm). Two vertical strips were cut from the edge of the membrane and stained with the reversible stain Pounceau S to visualize the immobilized protein. The membranes were then separately reacted with 10 ml of a 1:1000 dilution of one of the two polyclonal serum to identify the bands corresponding to the DHP subunits, i.e., one membrane was reacted with anti-β and the other was reacted with anti-γ. Peroxidase-conjugated second antibody was used to colorimetrically detect the cross-reacting bands. The sheep antiserum reacted with the $\alpha_1$ and β subunits; the guinea pig antiserum reacted with the γ subunit only.

Using the stained vertical strip as a guide, horizontal strips corresponding to the β and γ subunit proteins were cut from the immunoblot. To block non-specific binding sites on the nitrocellulose, the strips were incubated with BLOTTO (Bovine Lacto Transfer Technique Optimizer; 50 mM $NaH_2PO_4$, 150 mM NaCl, pH 7. 4, 5% Nonfat dry milk) for 1 hour at 22° C. The filters were then incubated overnight at 4° C. with 2 ml of either the β or γ polyclonal serum diluted with 8 ml of TBS-BSA (50 mM Tris.HCl 7.4, 150 mM NaCl, 3% BSA). The strips were then washed three times for 15 min each time in 500 mM NaCl, 50 mM Tris.HCl (7.4), followed by three sequential 15 min washes in 100 mM NaCl, 10 mM Tris.HCl (7.4). The bound antibody was eluted with 5 ml of acid (50 mM glycine HCl, pH 2.5) at a temperature of about 22° C. The pH of the eluted antibody wash was neutralized to 7.4 by the addition of 1.0M Tris.HCl, pH 8.0.

The affinity-purified antisera were characterized similarly to the polyclonal sera, and selection for sensitivity and subunit selectivity was done for antibody titer greater than 1:40. The βspecific antisera was called Affi-β, and the γ-specific antisera was called Affi-γ.

EXAMPLE 2

ANTIBODY SCREENING OF A RANDOM-PRIMED RABBIT SKELETAL MUSCLE cDNA LIBRARY AND CLONE CHARACTERIZATION

A. Library Screening

A rabbit skeletal muscle cDNA library was prepared in λgt11, as described by Ellis, et al. (1988), *Science* 241, 1661–1664, using random primers [pd(N)$_6$ hexamers (Pharmacia, Inc., Piscathaway, N.J.)] rather than oligo-d(T) to prime single-strand cDNA synthesis. Two sets of duplicate filters of the library, each containing 720,000 plaques, were made and screened for clones containing phage with inserts coding for all or part of the β and γ-subunits of the rabbit skeletal muscle calcium channel. Each filter was screened using either the β- or γ-specific antibody as follows. BLOTTO was used for blocking of the nitrocellulose filters, dilution of the antibodies, and filter washes. Detection involved horseradish peroxidase-linked rabbit anti-sheep secondary antibody and development proceeded using 4-chloro-1-naphthol as a substrate.

The λgt11 library was plated on Y1090 in LB agar and 50 μg/ml ampicillin. A Y1090 culture was grown overnight in 15 ml of LB, 0.2% maltose and 50 μg/ml ampicillin. The cells were pelleted and resuspended in 3 ml of 10 mM $MgSO_4$. Each of six plates was prepared by absorbing ~120,000 phage of the λgt11 cDNA library to 300 μl of the 3 ml cell solution and then pouring onto an LB agar plate in 10 ml soft agar containing 50 μg/ml ampicillin.

The plates were grown at 42° C. for 3.5 hours and then overlayed with IPTG-treated filters which were soaked in 10 mM IPTG (Boehringer Mannheim Biochemicals, Indianapolis, Ind.). The filters were dried until just moist, laid in the plates and incubated for 3.5 hours at 37° C. After the incubation, the filter was oriented, removed, and a second, identical IPTG-treated filter was applied to the agar plate for an additional four hours at 37° C. The orientation of this second filter was identified and marked identically to the first filter.

Two sets of six plates were prepared. One set of filters was used to screen for β-subunit encoding clones and the other set was used to screen for γ-subunit encoding clones. After incubation, one-half microgram of purified DHP receptor was spotted on one filter of each set as a positive control. The filters were washed for 30 min at room temperature with BLOTTO. One set of duplicate filters was then incubated with affinity purified sheep anti-β-subunit polyclonal antibody, and the other set was incubated with affinity purified guinea pig anti-γ-subunit polyclonal antibody. The filters were incubated with their respective antibody overnight in BLOTTO at 4° C. They were then washed three times, for 10 min each time, in BLOTTO.

The filters were then incubated for one hour with BLOTTO containing an appropriate second antibody: HRP-goat anti-sheep IgG (for β); or HRP-goat anti-guinea pig (for γ)].

The filters were washed as described above for the first antibody, and rinsed with $ddH_2O$ to remove BLOTTO.

The positive clones were developed using about 40 ml/plate of 4-chloro-1-naphthol reagent, which is made by dissolving 60 mg of said developer in 20 ml of ice cold MeOH and mixing 4-chloro-1-naphthol (Aldrich Chemical Company, Milwaukee, Wis.) into 100 ml of TBS containing 60μl of 30% $H_2O_2$.

Five positives were identified on both duplicate filters probed with the β antibody and two positives were identified on both filters probed with the γ antibody. Of the five putative β clones originally identified, two were characterized and used further: K5 and K6. Both of the γ clones were characterized: J6 and J10. The four clones were plaque-purified by replating and rescreening with the appropriate antibody using the same conditions as before, until a single, well-isolated plaque was identified for each clone.

B. Characterization of Putative β- and γ-Specific Inserts

The inserts of the putative β and γ clones were characterized by gel sizing, screening with antibody probes, restriction enzyme mapping, and partial sequencing.

1. Gel sizing

A mini-phage prep was made of each positive clone and the DNA was digested with EcoRI following manufacturer's instructions. The digests were then separated on a 1% agarose gel using the TAE buffer system (Maniatis, 1982), and HindIII digests of control λ DNA as size standards. Bands were visualized using ethidium bromide and u.v. illumination. Based on the results of gel analyses, the approximate size of the inserts were found to be as follows:

| | | | |
|---|---|---|---|
| K5 | 500 bp | J6 | 800 bp |
| K6 | 900 bp | J10 | 500 bp |

2. Restriction Enzyme Mapping

Figure 3:
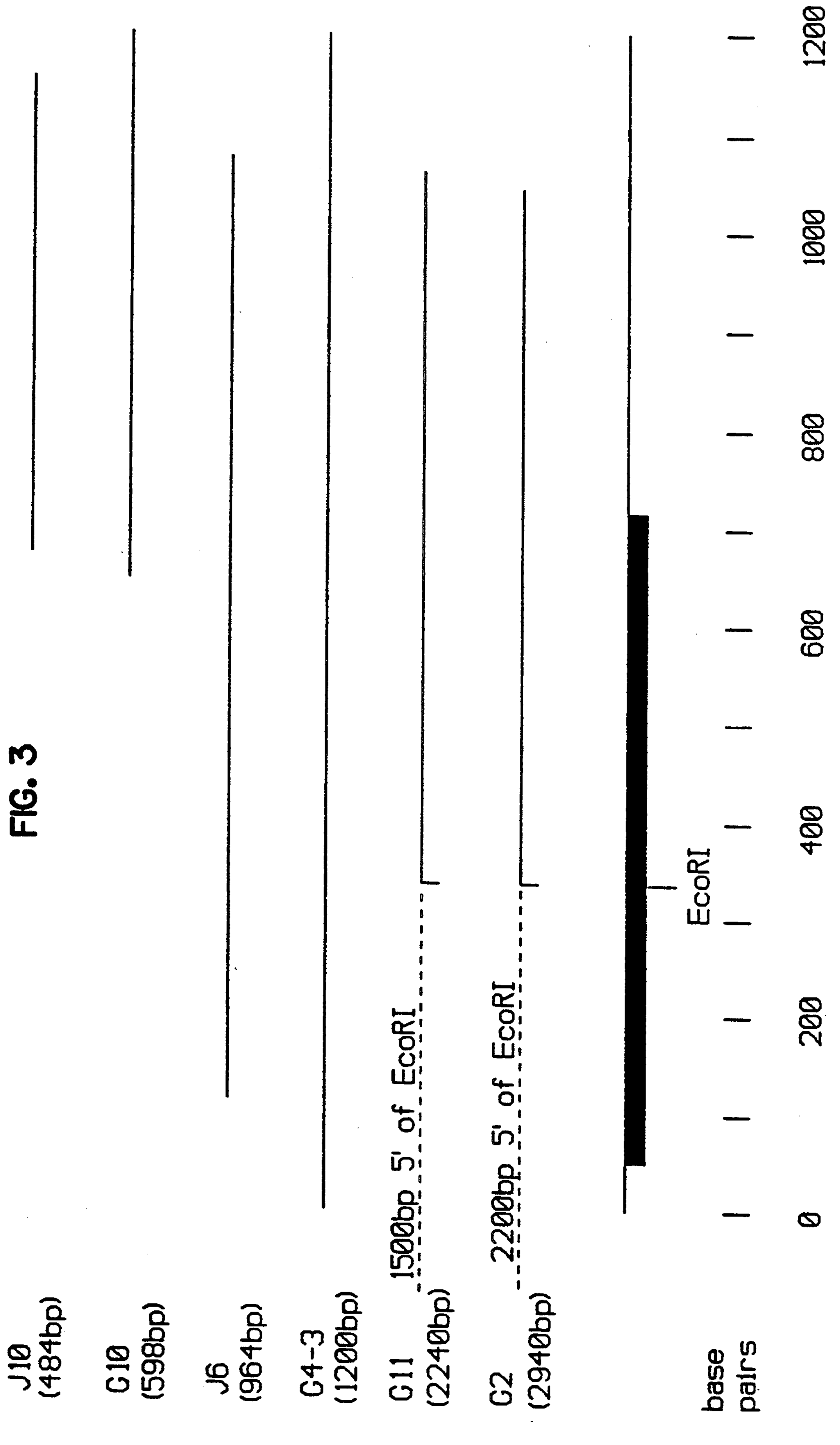
FIG. 3 is a restriction map of a cDNA sequence which encodes the γ-subunit of a calcium channel, and shows the orientation of various cDNAs encoding the γ-subunit sequence.
Figure 5A:
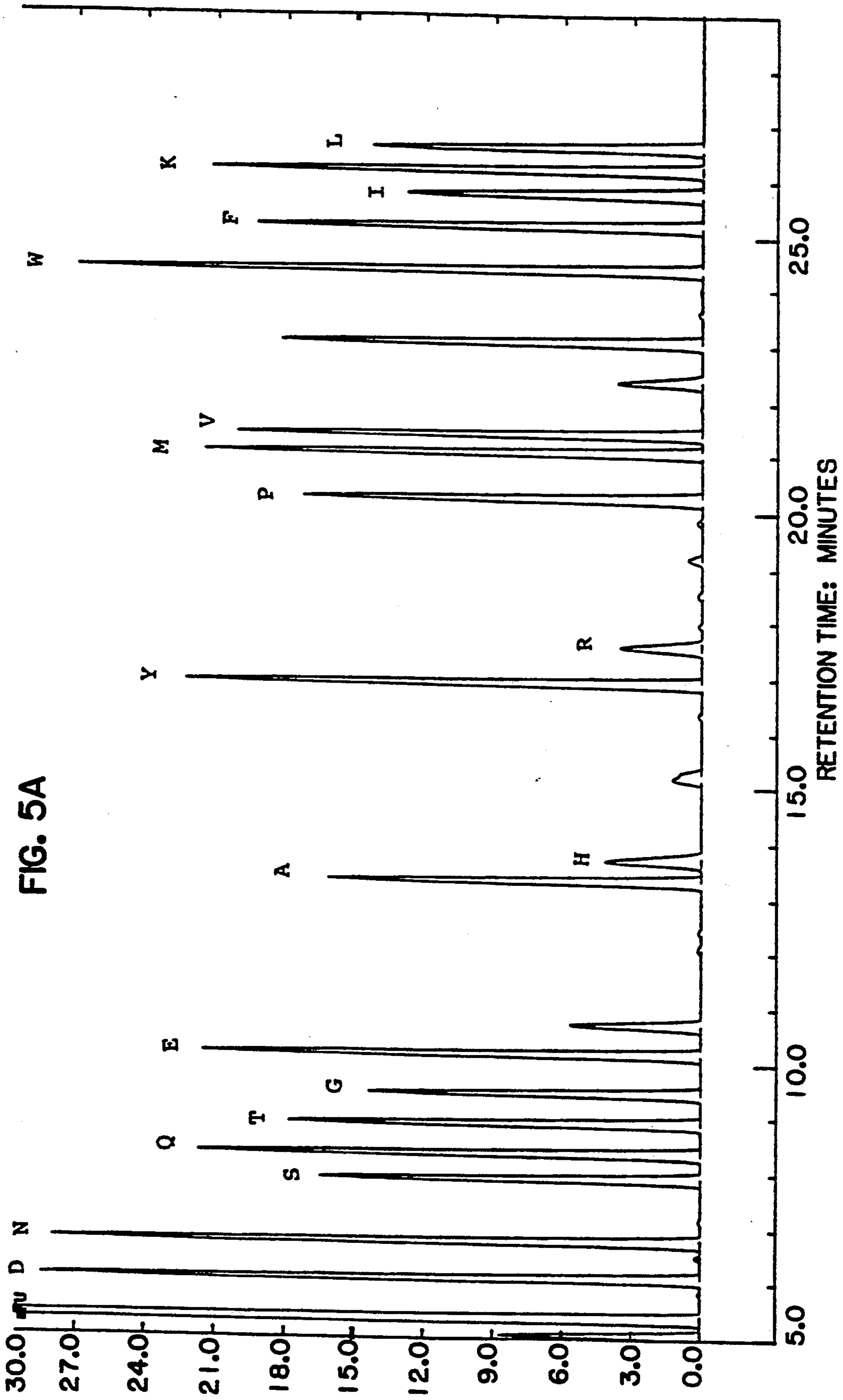
FIG. 5 provides raw data from which the amino acid sequence for the first nine residues at the N-terminus of the γ-subunit of a calcium channel was ascertained.
Figure 5B:
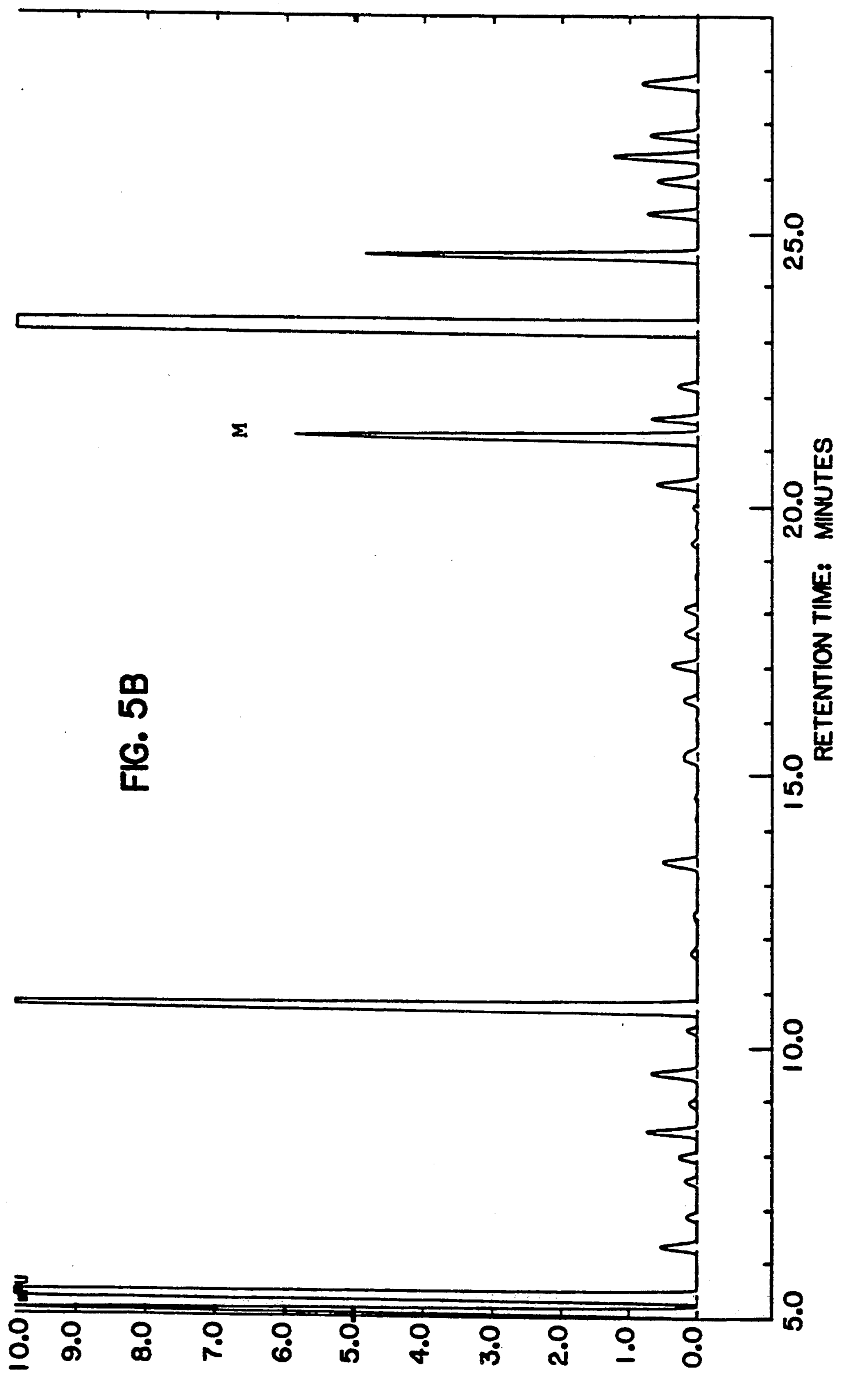
Figure 5C:
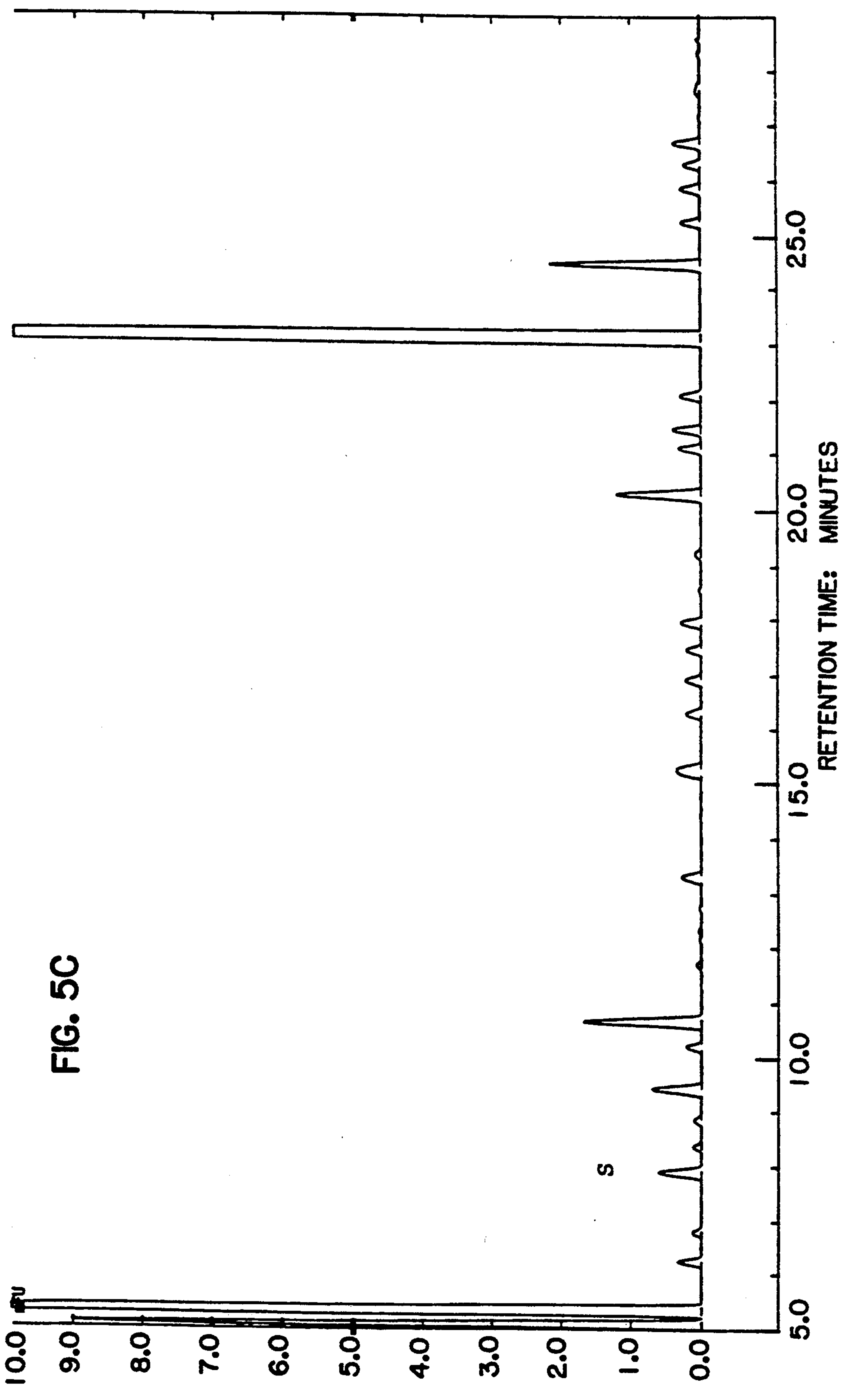
Figure 5D:
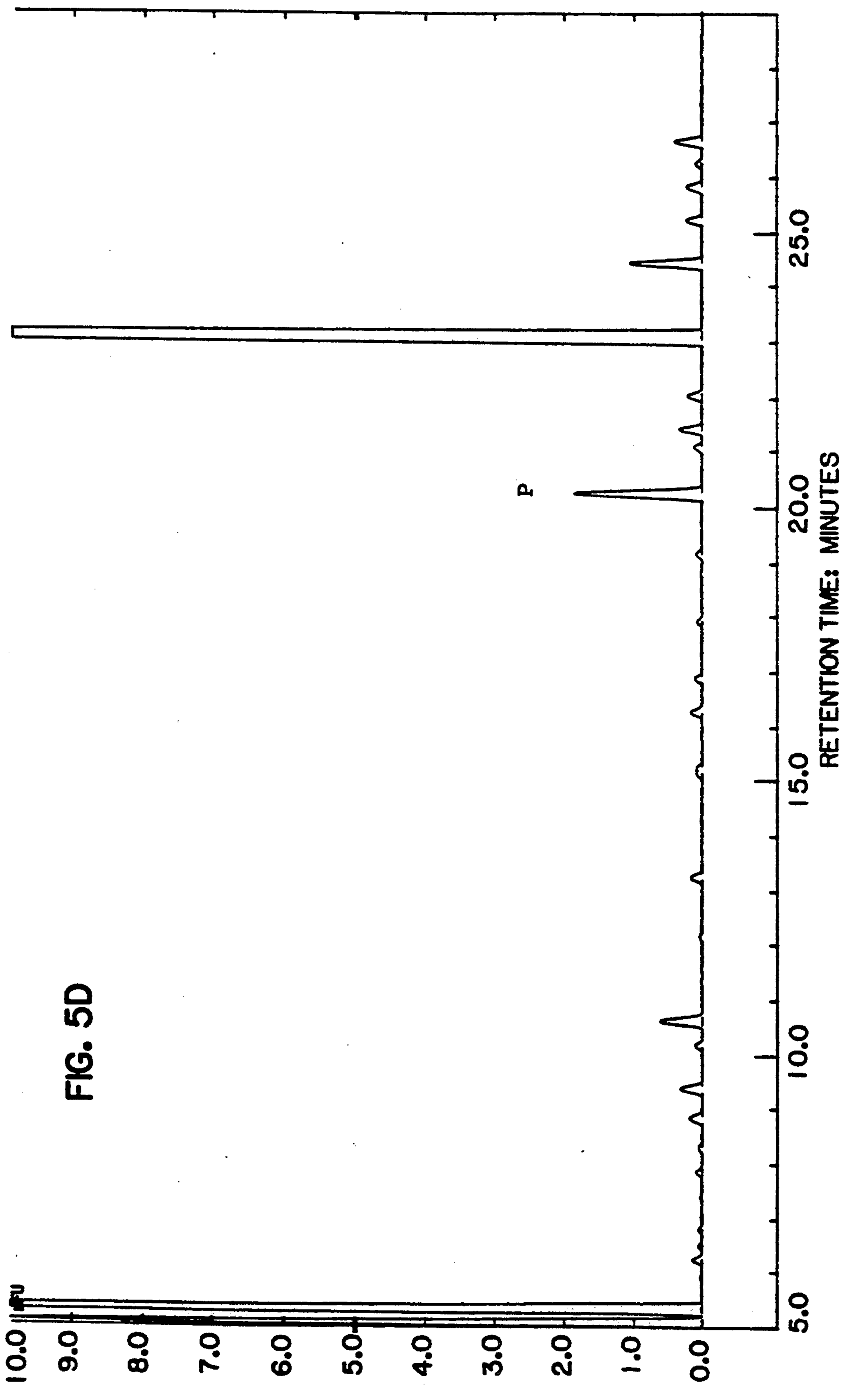
Figure 5E:
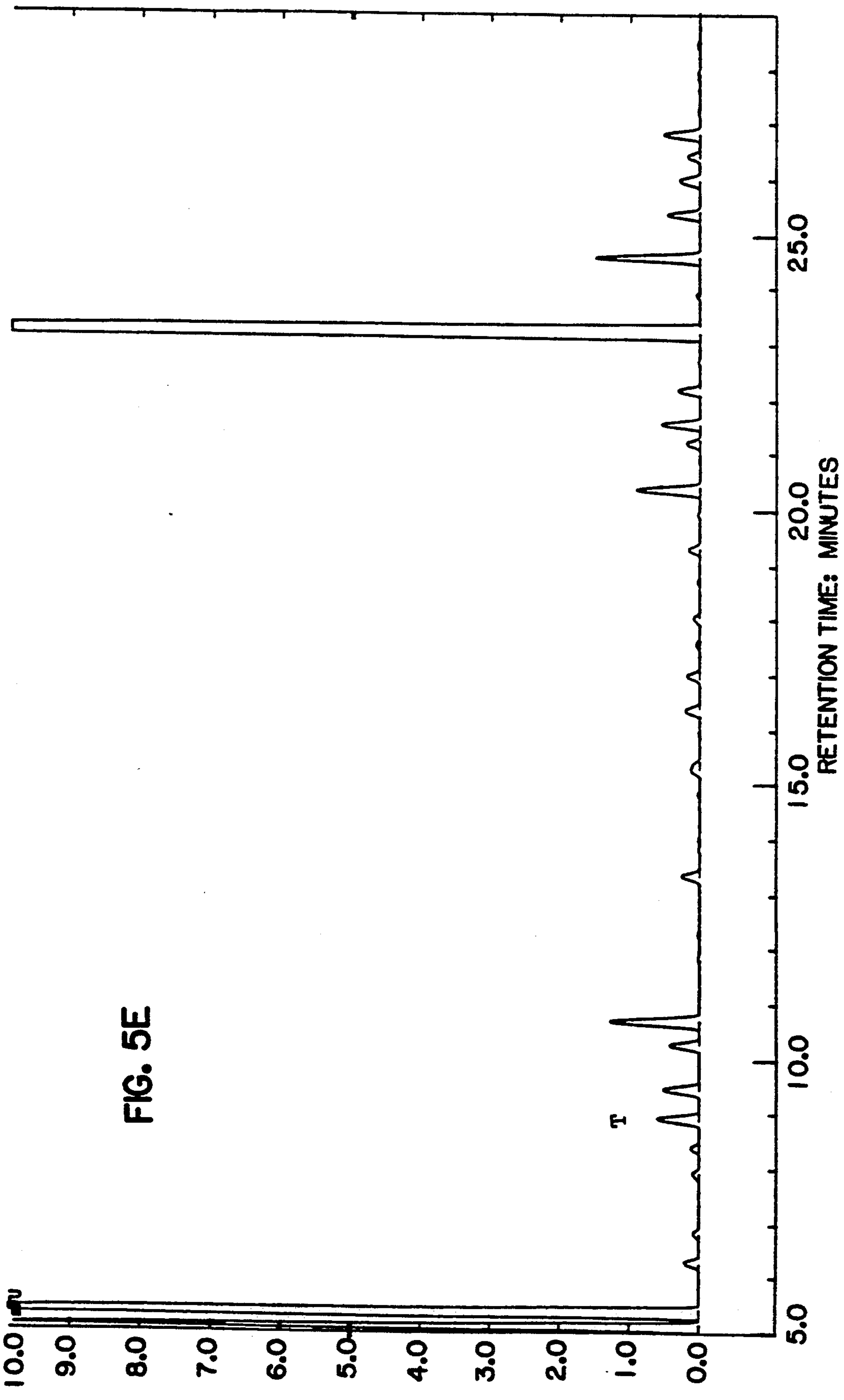
Figure 5F:
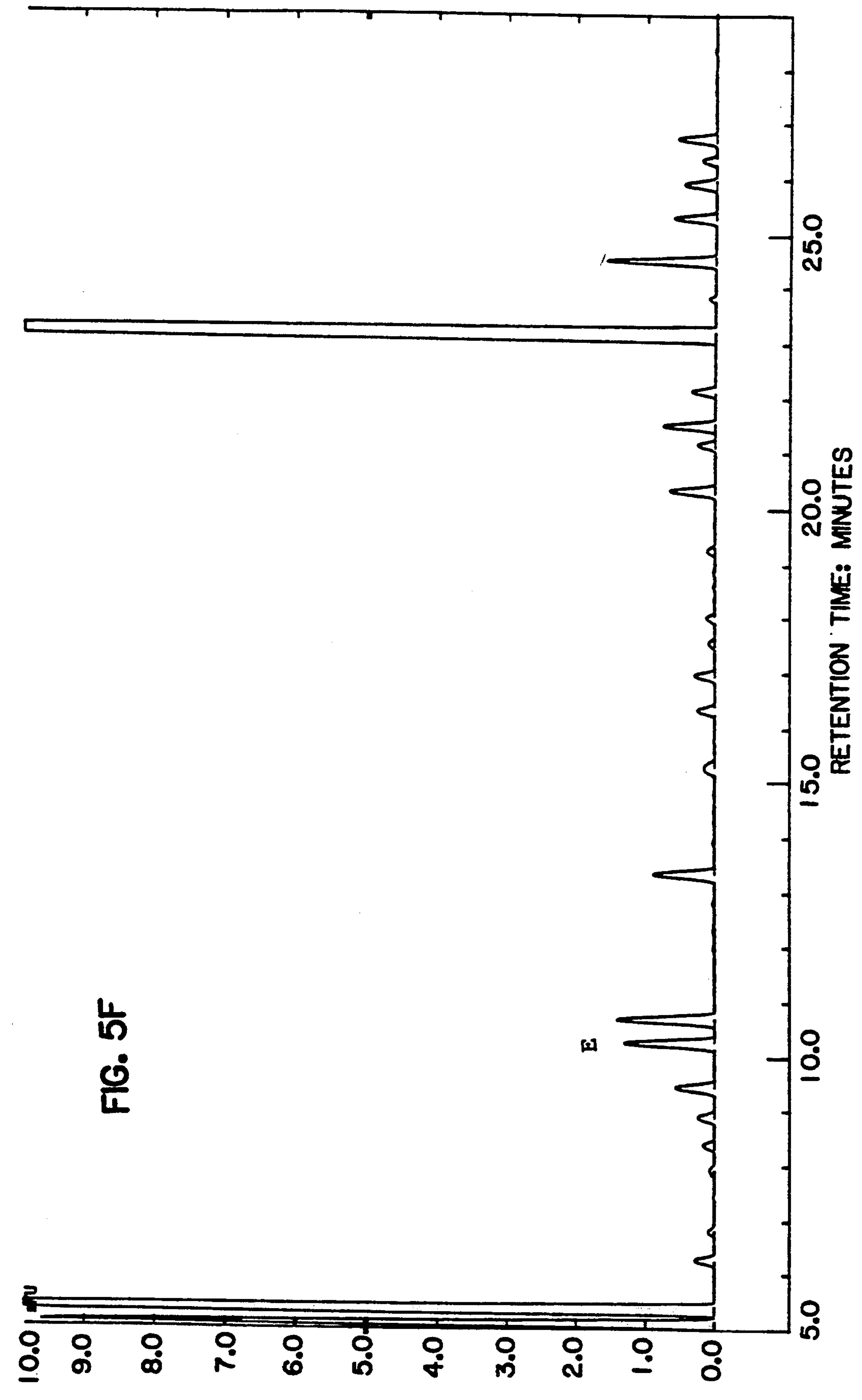
Figure 5G:
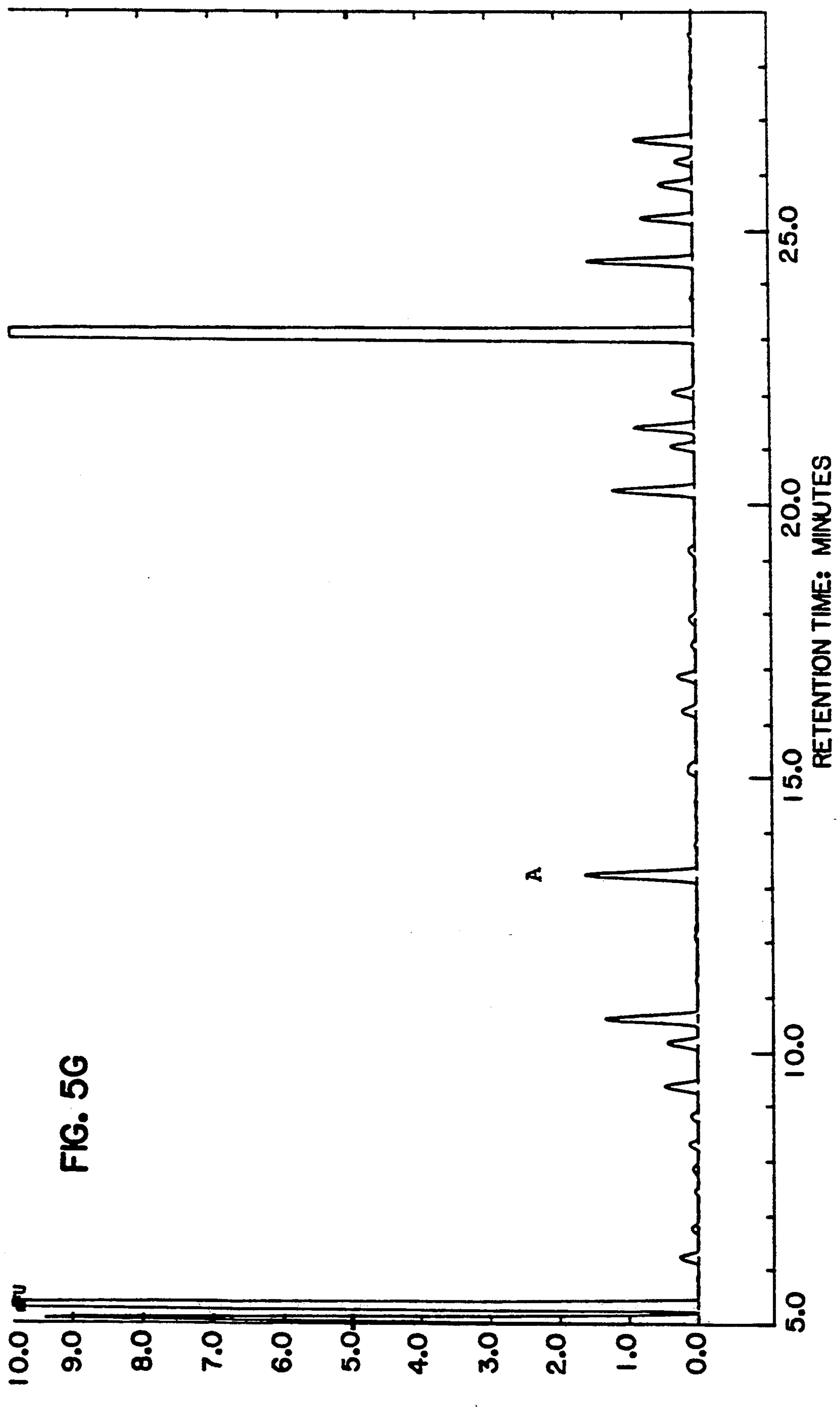
Figure 5H:
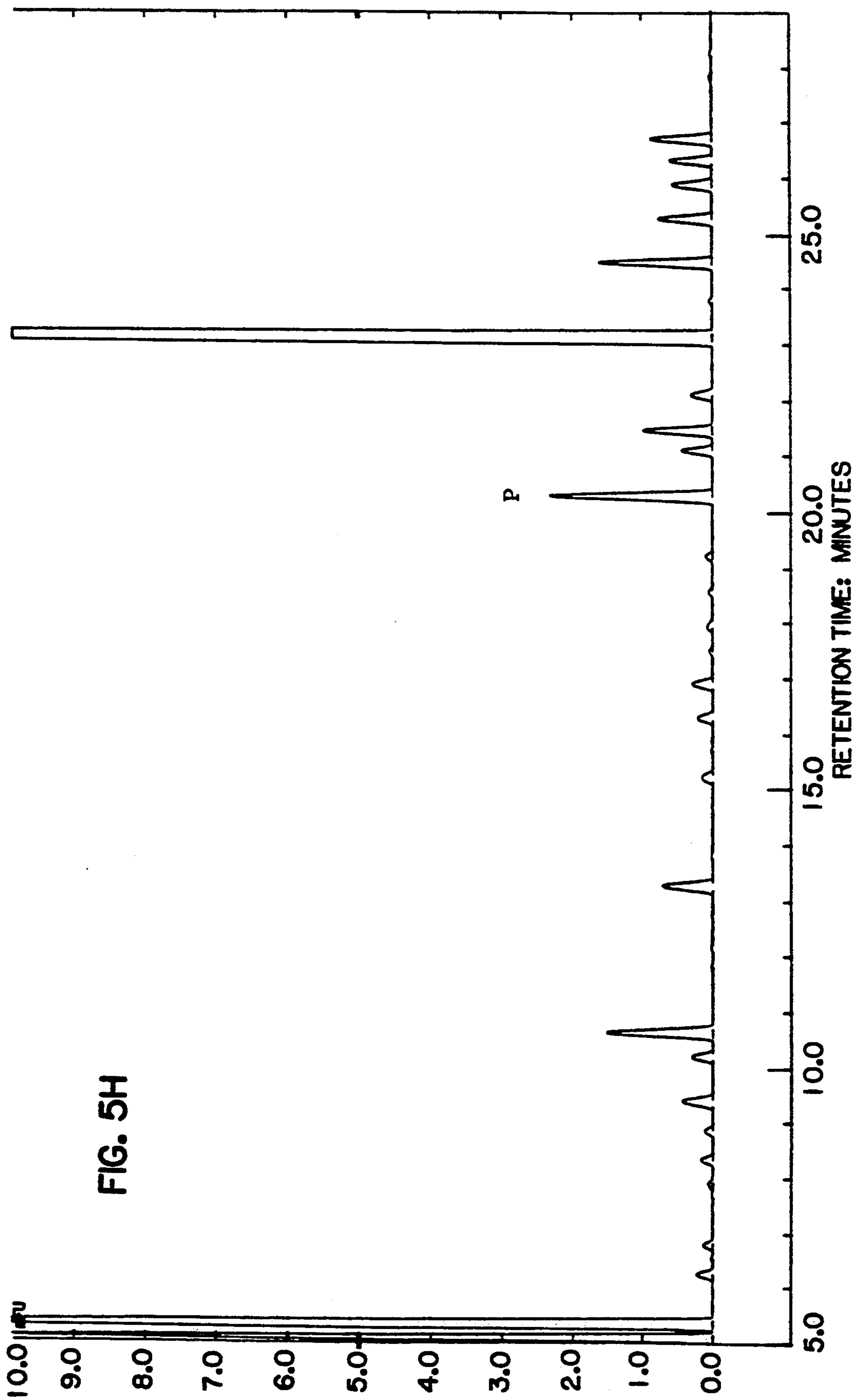
Figure 51:
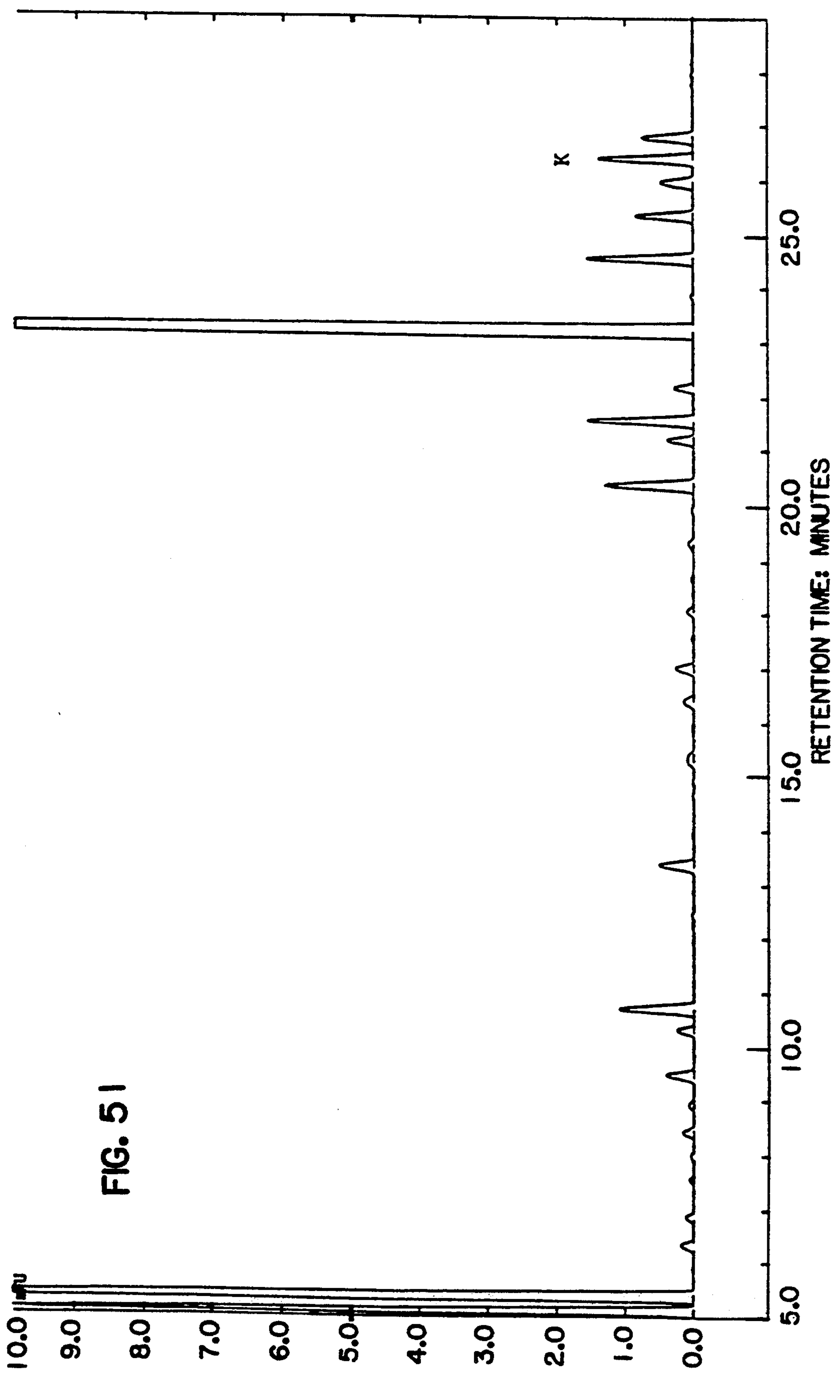
Figure 5J:
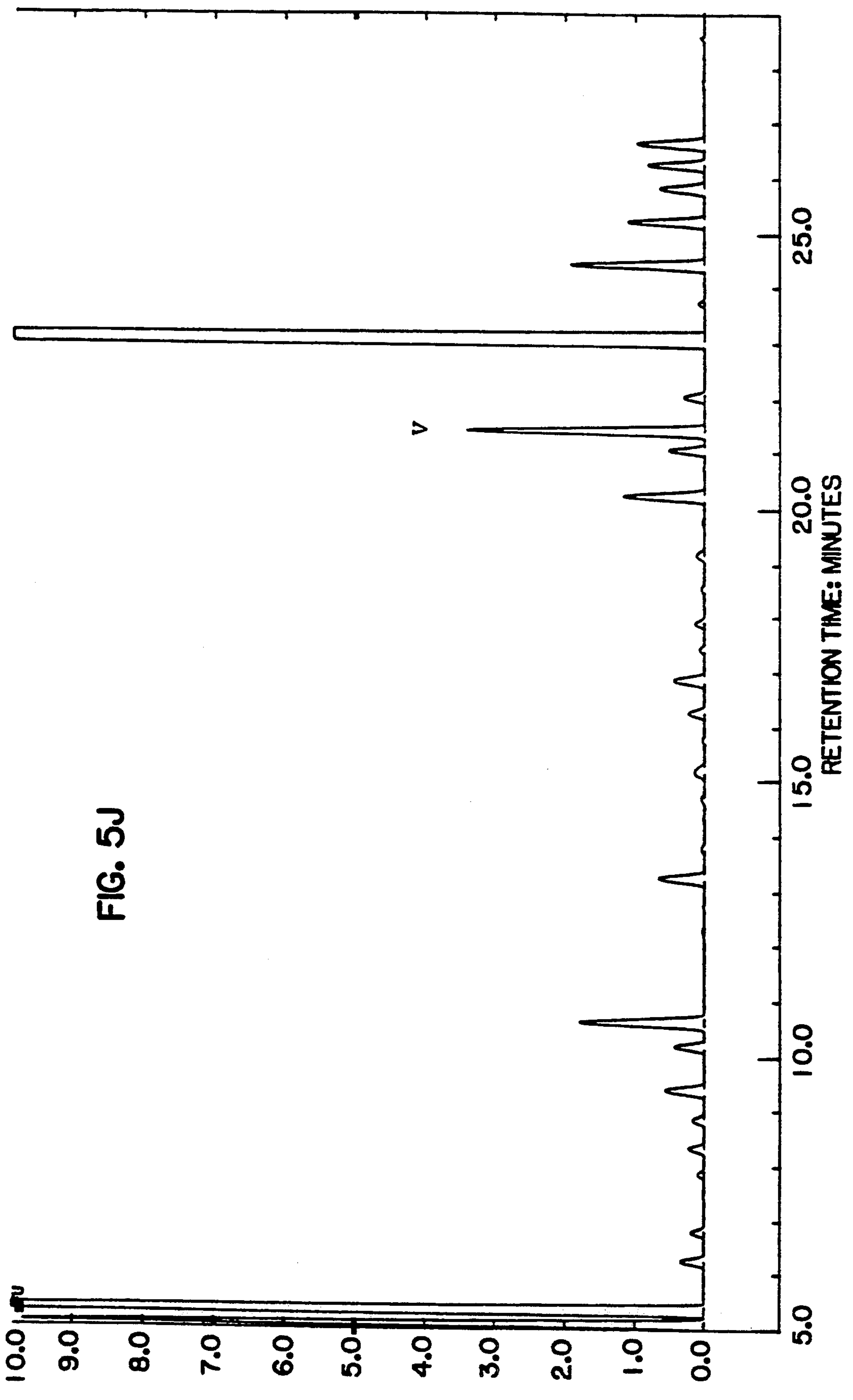

To further characterize the inserts of the putative β and γ clones, the inserts were restriction mapped. The EcoRI inserts were subcloned into EcoRI-cut, bovine alkaline phosphatase (BAP)-treated modified pUC19 plasmid. The modified pUC19 plasmid was made by digesting pUC19 with HincII and SmaI and ligating the blunt ends. The resultant plasmid was 17 bp shorter than pUC19 and lacked several restriction sites, i.e., SmaI, XmaI, BamHI, XbaI, HincII, AccI, and SalI. Ten micrograms of the ligation reaction were used to transform DH5α cells. AmpR colonies were selected. Plasmid preps were made from the amp$^R$ colonies and aliquots of the DNA were separately digested with selected restriction enzymes. The maps of inserts of the β and γ clones are shown in FIGS. 2 and 3, respectively.

3. Antibody probes screen

Plasmid-containing bacteria were grown overnight on ampicillin plates (having a colony density of about 100 colonies per plate). Replicate lifts were made using dry untreated nitrocellulose filters. The replicate lifts were then incubated for 3 hours at 37° C. on filter paper wetted with LB Media plus 10 mM IPTG. Incubation was carried out with filters maintained in an inverted position to induce the production of fusion proteins.

Cells were lysed by exposing the filters to chloroform saturated vapors for 5 minutes, followed by overnight incubation at 4° C. in BLOTTO containing 10 mg/ml lysozyme. The filters were then immunoblotted with the appropriate antibodies using the methods described above.

a. β-specific clones

Both clones tested positive with the affinity-purified antisera Affi-62 . Additionally, only clone K5 tested positive with β-specific monoclonal antibody VD21 [Leung, et al, *J. Biol. Chem.* 263,994–1001 (1988)].

b. γ-specific clones

Neither of the two γ-specific clones reacted with antisera specific for the $\alpha_1$-, $\alpha_2$-, β-, or δ-specific antisera.

4. Partial Sequencing a. β-specific inserts

A large scale plasmid prep of K5 was prepared, and 2 g of the DNA per reaction was sequenced according to the procedure provided by United States Biochemical Corporation (Cleveland, Ohio; Sequenase DNA Sequencing Kit). The M13 reverse sequencing primer and the M13 sequencing primer (New England Biolabs, Inc. Beverly, Mass.) were used to prime the sequencing reactions.

Partial sequence of K6 was obtained by isolating two clones comprised of the K6 insert in the modified pUC19 vector in both orientations. The ends of the insert were sequenced using the reverse and forward M13 primers as described for K5. Then, using the SacI site 255 bp from the 5′ end of K6 and the HindIII site 444 bp from the 3′ end of the insert, in combination with the same restriction sites in the polylinker, deletions in K6 were generated and internal sequence was determined. For each restriction site there are two possible orientations and, thus, two deletions that could be generated. For example, the 255 bp SacI fragment can be released and the remaining DNA religated in order to generate sequence beginning 255 bp in from the 5′ end. With the fragment in the opposite orientation, the remaining 684 bp SacI fragment can be released and sequence can then be generated beginning 684 bp in from the 3′ end. Each of these deletions was generated (two for the SacI site and two for the HindIII site) and the entire K6 fragment was sequenced.

Analysis of the sequence data revealed a 167 bp overlap between clones K5 and K6, as well as predicted restriction enzyme recognition sites. The K6 insert was predicted to have at least one internal restriction site for the enzymes HindIII, SacI, and PstI. A single open reading frame is encoded by these two overlapping clones. No initiating ATG triplet or translation stop codon was identified. Based on the β-subunit size of 52 kDa and a predicted coding region of at least 1400 bp, the isolated inserts were at least 150 bp short of being complete.

b. γ-specific insert

The 484 bp EcoRI insert fragment was isolated from a large-scale preparation of J10 and subcloned into pGEM-3 (Promega Corp., Madison, Wis. 53711). pGEM-3 contains both the T7 and SP6 polymerase binding sites positioned on opposite ends of the polylinker sequence. Oligonucleotide primers specific for these polymerase binding sites were purchased from New England Biolabs, Inc. (Beverly, Mass. 01915). The J10 insert sequence was determined by sequencing in from each end of the insert directly out of the plasmid DNA. The Sequenase Kit was used as described above. Overlapping sequence at the center of the insert was observed, thus, the sequence of the entire insert was complete.

The J6 insert contains an internal EcoRI restriction site that divides the insert into two fragments, a ~740 bp fragment and a ~230 bp fragment. Initially, the larger, 740 bp fragment was subcloned into the modified pUC19 vector. The ends of the insert were sequenced using the universal and reverse primers described above, and J6 was positioned relative to J10 based on the determined sequence.

Oligonucleotide primers were synthesized based on the terminal sequences of J10. Internal J6 sequence was determined using the γ-specific oligonucleotide primer based on the 5′ end of J10. This determined sequence combined with the J10 sequence, completed the sequencing of the 740 bp J6 fragment and provided 819nts of continuous sequence.

To characterize the remaining sequence, the ~230 bp J6 EcoRI fragment was subcloned into pGEM-3 and sequenced.

EXAMPLE 3

SCREENING OF OLIGO dT-PRIMED RABBIT SKELETAL MUSCLE cDNA LIBRARY AND CLONE CHARACTERIZATION

A. Screening

In an attempt to isolate inserts encoding the full length β- and γ-specific cDNA, or at least to isolate inserts encoding β- and γ-specific cDNA sequences that could be spliced to inserts from clones K5 and K6, and J6 and J10 to construct full length β- and γ-specific cDNAs, respectively, the inserts from clones K5 and K6, and J6 and J10 were used to screen two pairs of duplicate lifts of an oligo dT-primed rabbit skeletal muscle λgt11 cDNA library (Ellis, et al., Supra) under non-stringent conditions. Hybridization: 20% formamide, 5× Denhardts, 6× SSPE, 0.2% SDS, at 42° C. Wash: 0.2× SSPE, 0.2% SDS, 45° C.

Screening with the β inserts yielded four positives on duplicate filters. The γ insert screening yielded three positives on duplicate filters. The seven clones were plaque-purified and remained positive in subsequent screenings.

B. Characterization

The inserts from the positive clones were removed by EcoRI digestion as described previously and sized. The clone names and insert sizes are as follows:

| | | | |
|---|---|---|---|
| βB | 1800 | G2 | 2300 |
| βC | 1500 | G11 | 2000 |
| βD | 1500 | G10 | 650 |
| βE | 2100 | | |

The inserts listed above were subcloned into pUC19, modified as before, and restriction mapped and partially sequenced. The restriction maps allowed the various β and γ clones to be oriented [as shown in FIGS. 2 and 3].

The DNA sequence of insert βD was determined directly out of the plasmid using the M13 primers as described previously. Insert βD is 1293 bp. It extends 218 nts 5′ of K5 and ends 176 nts short of the 3′ end of K6 (See FIG. 2).

The sequence of the βE insert at the 3′ end was determined by sequencing the plasmid DNA priming with the universal primer (sequencing through the polyA tail) and priming internal sequence using an oligo synthesized based on the 3′ end of K6. Overlapping sequence was determined, thus completing a continuous 1769 nt sequence from the 5′ end of βD to the 3′ end of βE.

The sequence at the 3′ end of βB was determined as described above. The sequence primed with the internal oligo matches the sequence determined for βE. Sequence adjacent to the polyA tail was obscured and not determined. Even though individual nucleotides cannot be determined in this sequencing reaction, one can see from the general pattern that the sequence matches the sequence determined for βE.

FIG. 4 shows the complete DNA sequence and deduced amino acid sequence of the cloned β-subunit transcript. This sequence is a compilation of the DNA sequence determined by us and that reported by Ruth et al., *Science* 245, 1115 (1989). Ambiguities in the sequence determined by us were resolved by comparison of the sequence to that reported by Ruth et al. The amino acid residue through these regions are shown circled.

The termini of clone G10 were sequenced as described above and G10 was positioned relative to J6 and J10. A polyA tail was identified at the 3′ end. Overlapping sequence was completed by priming G10 sequence internally using an oligonucleotide primer based on the 3′ end of J10. The combined, determined sequence of J10, J6, and G10 was 1139 nt.

EXAMPLE 4

SCREENING OF OKAYAMA-BERG RABBIT SKELETAL MUSCLE cDNA LIBRARY FOR γ-SUBUNIT INSERTS AND CLONE CHARACTERIZATION

A rabbit skeletal muscle cDNA library (MacLennan et al., 1985, *Nature* 316, 696) constructed according to Okayama and Berg was screened for γ clones. Approximately $2\times10^6$ recombinants were transformed into *E. coli* by standard methods. The transformation mix was divided into ten aliquots and each was separately inoculated into 100 mls of broth media. The transformed *E. coli* were grown to stationary phase and the plasmid DNA in each of the ten cultures was recovered by a standard plasmid prep procedure that was scaled down to 100 mls. Digestion of the pools with BamHI or XhoI released the insert from the Okayama-Berg vector pcD-X. The digest was probed with the J10 insert fragment. A series of fragments, the largest and most abundant fragment being ~1.5 kb for XhoI and ~1.4 Kb for BamHI were identified. These insert sizes are consistent with an ~1200 nt transcript (see below) after additional sequence contributed by the Okayama-Berg vector, ~250 nt for XhoI and ~150 nt for BamHI, is subtracted. These fragments were present in both pool 8 and pool 10.

An aliquot of pool 8 was transformed into *E. coli* and ~600,000 recombinants were probed with the J10 fragment. Approximately ~50 to 75 duplicate positives were identified. Nine were chosen for further characterization. The insert size was identified in two clones: G4-3 and G6-1, ~1275 nts and ~1075 nts, respectively. The internal EcoRI site was mapped in each clone. G4-3 extends ~475 nt 5′ of the EcoRI site and 6-1 extends ~275 nts 5′ of the site. Further characterization of G4-3 by subcloning into M13 and DNA sequencing showed that G4-3 encoded the complete γ-subunit coding sequence in addition to 48 nt of 5′ untranslated sequence and 457 nt of 3′ untranslated sequence. The γ-subunit cDNA sequence and the determined amino acid sequence are shown in FIG. 1.

EXAMPLE 5

SEQUENCE OF THE γ PROTEIN ISOLATED FROM RABBIT SKELETAL MUSCLE TISSUE

The γ-subunit protein was electrophoresed and blotted onto immobilon by the method of Matsudaira [*J. Biol. Chem.* 262, 10035–10038 (1987)]. The portion of the blot that contained the γ-subunit was excised from the immobilon membrane and analyzed for protein sequence. The stained immobilon pieces were placed into a sequencing reaction chamber above a biobrene-treated glass fiber filter. The Applied Biosystems 470 Gas Phase Protein Sequencer, with online phenylthiohydantoin analyzer, was run as described previously [Hunkapillar, M. W. and Hood, L. E. (1983), *Science* 219, 650; Hewick, R. M. et al., *J. Biol. Chem.* 256, 7990 (1981)], and the following sequence was determined:

```
1           5           9
M—S—P—T—E—A—P—K—V
```

The raw data for this sequencing analysis is presented in FIG. 5.

EXAMPLE 6

DEVELOPMENT OF CALCIUM CHANNEL SUBUNIT-EXPRESSING MAMMALIAN CELLS

A. Transient Transfection Protocol

The host cells transfected with calcium channel subunit-encoding DNAs, transfection selection plasmids, and marker construct plasmid were developed using the following protocol.

Approximately 24 hr prior to transfection, host cells are plated in 10 cm plates at a density of $2.5\times10^6$ cells/-plate and incubated at 37° C. (5% $CO_2$). One to eight hours prior to transfection, the cells are fed 9 ml of media [500 ml Dulbecco's Modified Eagle Medium; 4500 mg/L D-glucose; L-glutamine; 55 ml calf serum; 5 ml penicillin/streptomycin (100×: 10,000 U/ml/10,000 μg/ml) ].

The DNAs are prepared by combining 5 μg of each subunit-encoding expression plasmid to be transfected with water to a final volume of 440 μl. The water-DNA solution is mixed, and 60 μl of 2M $CaCl_2$ is added and mixed. This is called Solution B. Solution A is 500 μl of 2×HBS (2×=10 g/L Hepes, 16 g/L NaCl; autoclaved; pH=7.10±0.05) mixed with 10 μl of $100\times PO_4$ (1:1 mixture of 70 mM $Na_2HPO_4$ and 70 Mm $NaH_2PO_4$. A DNA precipitate is made by dripping Solution B into Solution A, while bubbling sterile air through Solution A for mixing. The precipitate is allowed to form during the next 30±10 min.

The plated cells were transfected by adding, dropwise, ~1 ml of precipitate to each plate containing cells and media and mixing well by swirling. The treated cells were returned to the incubator (37° C.; 5% $CO_2$) for five hr.

A glycerol shock is then applied to the transfected cells by removing the DNA precipitate and media and adding 2 ml of media containing 10% glycerol. After three minutes, the glycerol media is diluted with 5 ml PBS and mixed. The PBS-diluted media is aspirated off and the 5 ml PBS wash is repeated two more times.

After the third PBS wash is aspirated off, the cells are fed 9 ml media and incubated at 37° C. (5% $CO_2$) for 24 to 72 hr.

The transfected cells can be analyzed 24–72 hours after DNA addition. Analysis can include 1) selection of transfectants, 2) northern analysis, 3) western analysis, 4) ligand binding studies, 5) functional analysis using a marker construct, and 6) electrophysiological measurements.

B. Mammalian Host Cells

The preferred cells for use as host for transfection with DNAs of the invention are Ltk-cells (ATCC CCL1.3).

C. Eukaryotic Expression Vectors Encoding Calcium Channel Subunit-Encoding DNAs The calcium channel subunit expression plasmids were constructed using the following parent plasmids: (1) modified pSV2dhfr [Subramani et al., (1981) *Mol. Cell. Biol.* 1:854–864; modified by cutting at the unique HindII site and inserting a 5′ -EcoRI-EcoRV-HindIII-3′ polylinker], (2) pSV2 (plasmid pSV2dhfr was digested with HindIII and BglII, releasing the dhfr sequence, which was then replaced with a 5′ -HindIII-EcoRV-EcoRI-BglII-3′ adapter), and (3) pcD-X [Okayama, H. and Berg, P. (1983) *Mol. Cell. Biol.* 3:280–289].

Figure 6:
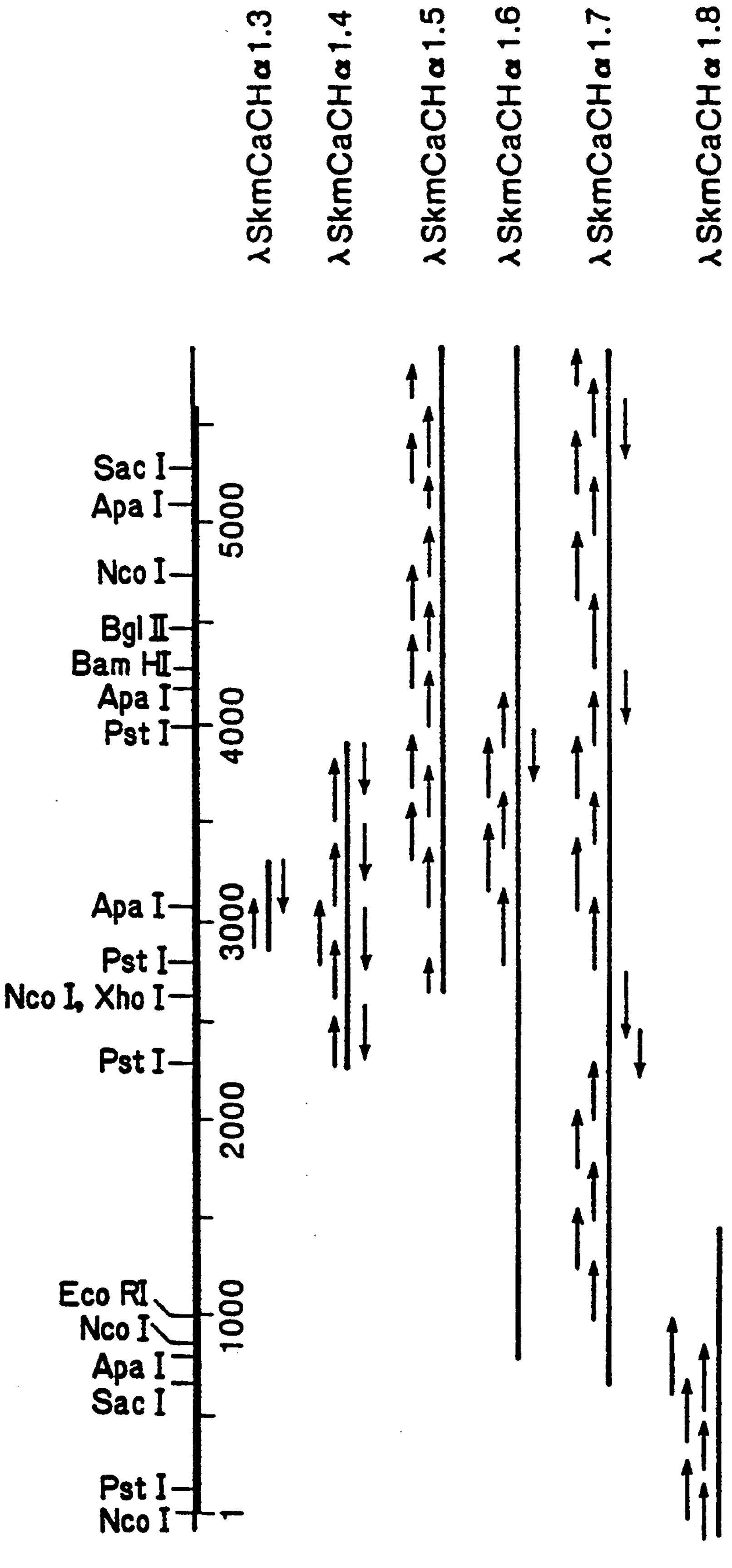
FIG. 6 is a restriction map of a cDNA sequence which encodes the $\alpha_1$-subunit of a calcium channel, and shows the orientation of various cDNAs encoding the $\alpha_1$-subunit sequence.
Figure 7:
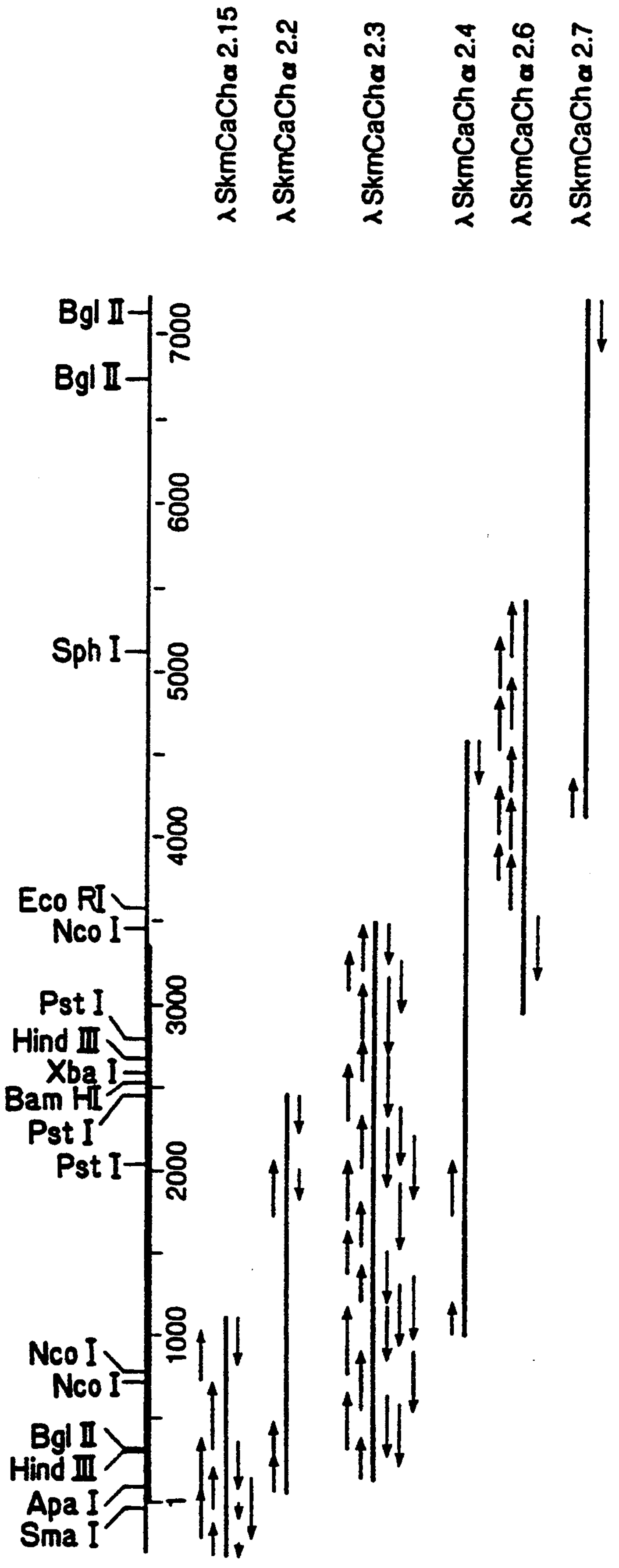
FIG. 7 is a restriction map of a cDNA sequence which encodes the $\alpha_2$-subunit of a calcium channel, and shows the orientation of various cDNAs encoding the $\alpha_2$-subunit sequence.

For each expression construct, the insert and vector were ligated at approximately a 2:1 insert-to-vector molar ratio, generally using 50 to 100 ng of vector. Restriction maps of the α1, α2 and β clone inserts, referred to in 1 and 2 below, are shown in FIGS. 6, 7 and 4, respectively.

1. pSKmCaCHα1pSV2dhfr

The 1.55 kb KpnI (polylinker sites) fragment from clone λSKmCaCHα1.8 [Ellis et al., (1988); *Science* 241: 1661–1664)] was inserted into a plasmid vector (e.g., pIBI24, pUC18, pUC19), and the KpnI-EcoRI fragment, encoding nucleotides −78 to 1006 of the α1 subunit, was gel purified.

The 4900 bp EcoRI-BamHI (BamHI site in pcD-X vector) fragment from clone pSKmCaCHα1.7 (Ellis et al., supra) was isolated and gel purified. The BamHI digest was a partial digest to avoid cutting at the internal BamHI site located at ~4300 bp. This fragment was subcloned into EcoRI-BamHI-digested pIBI24 (International Biotechnologies, Inc.; New Haven, Conn.), and the ~4900 nt 3′ EcoRI-XbaI (XbaI polylinker site) fragment from that plasmid was gel purified.

The ~1085 nt fragment originating from ~SKmCaCHα1.8 was ligated to the ~4900 nt fragment originating from pSKmCaCHα1.7, and the ligation was cloned into KpnI-XbaI-digested pGEM3 (Promega Corp., Madison, Wis. 53711). An upstream ATG present in the ligated insert, contributed by the EcoRI-KpnI-NcoI adapter used to construct the library from which λSKmCaCHα1.8 was isolated, was removed as follows. The plasmid (pGEM3+ insert) was linearized with KpnI, and the linearized DNA was digested with T4 polymerase in the dCTP; this limits the digestion in both directions to the first C nucleotide. The ends were then made blunt by digestion with S1 nuclease. The linear DNA was ligated to itself and transformed into DH5α cells. The deletion was confirmed by sequencing. This clone was called pSKmCaCHα1.1ΔNcoI.

Modified vector pSV2dhfr was digested with EcoRI and HindIII. A partial EcoRI digest and a HindIII digest of clone pSKmCaChα1.1ΔNcoI was performed, and the ~5950 bp insert encoding the α1 subunit was isolated on a low percentage agarose gel. The vector and insert fragments were ligated together and transformed into DH5α cells. AmpR cells were selected. Correct plasmid was confirmed by restriction mapping and was called pSKmCaCHα1pSV2dhfr. It contains the coding sequence of the α1 subunit of the rabbit skeletal muscle calcium channel, preceded by approximately 78 nucleotides of 5′ sequence and followed by the 3′ untranslated sequence and a stretch of As.

2. pSKmCaCHα2pSV2

Equal molar amounts of the 650 bp KpnI-HindII fragment from λSKmCaCHα2.15 and the 2700 bp HindIII-XbaI fragment from λSKmCaCHα2.3 (both described in Ellis et al., supra) were ligated together with 50 ng of KpnI-XbaI-digested and dephosphorylated pIBI24. The ligation was transformed into competent NM522 cells (Stratagene, Inc., San Diego, Calif.) and AmpR colonies were selected. The correct clone was identified by restriction mapping and was called pα2.1. Clone pα2.1 was digested with XbaI and SphI (SphI site in vector) and dephosphorylated. A second three-way ligation was performed with the XbaI-SphI fragment from pα2.1 and the 750 bp XbaI-NcoI fragment from λSKmCaCHα2.3 and the 1800 bp NcoI-SphI fragment from λSKmCaCHα2.6. The ligation was transformed into NM522 cells and AmpR colonies were selected. Correct plasmid was identified by restriction digest mapping and was called pα2.15.

Vector pSV2 was digested with EcoRI and EcoRV and ligated to the ~3600 bp gel purified, SmaI-EcoRI fragment from pα2.15. The ligation was transformed into DH5α cells. AmpR cells were selected. Correct plasmid was identified by restriction digestion, and was called pSKmCaCHα2pSV2. It contains the coding sequence of the α2 subunit of the rabbit skeletal muscle calcium channel, preceded by approximately 56 nucleotides of 5′ sequence and followed by ~300 nt of 3′ untranslated sequence.

3. pSKmCaCHαpSV2

A full-length construct of the β-encoding sequence was made by ligating the 975 bp EcoRI-HindII fragment (5′ end ofβ) from pβD (gel-purified) and the 775 bp HindIII-EcoRI fragment (3′ end of β) from pβB (gel purified) together. The ligation was then digested with EcoRI and the 1700 bp EcoRI fragment was gel purified and ligated into EcoRI-digested and dephosphorylated pGEM3Z. The ligation was transformed into DH5α cells, and restriction mapping was performed to identify the correct clone. The 1700 bp insert of the correct clone was released by EcoRI digestion, gel purified, and ligated into EcoRI-digested and dephosphorylated vector pSV2. The ligation was transformed into DH5α cells. AmpR cells were selected. Correct plasmid was identified by restriction mapping and was called pSKmCaCHβpSV2. It contains the coding sequence of the β subunit of the rabbit skeletal muscle calcium channel, preceded by approximately 92 nucleotides of 5′ sequence and followed by 3′ untranslated sequence and a stretch of As.

4. pSKmCaCHγpcD-X

Clone G4-3, isolated from the Okayama-Berg library (see Example 4), was renamed pSKmCaCHγpcD-X. It contains the coding sequence of the γ subunit of the rabbit skeletal muscle calcium channel, preceded by approximately 48 nucleotides of 5′ sequence and followed by 3′ untranslated sequence and a stretch of As. The insert is contained in the pcD-X expression vector.

D. Development of Cell Line Containing Four Calcium Channel Subunit DNAs

Cells were developed to express all four subunits of a calcium channel by transfecting Ltk-cells with 5 μg each of plasmids pSKmCaCHα1pSV2dhfr (α1),pSKmCaCHα2pSV2 (α2), pSKmCaCHα1pSV2 (γ),pDKmCaCHγpcD-X (β), and 1 μg of the selection plasmid pThx24 [Zipser et al. (1981); *Proc. Natl. Acad. Sci.* 78:6276–6280], following the protocol of (A). Positive transfectants were selected in HAT media (media in "A", plus 15 μg/ml hypoxanthine, 1 μg/ml aminopterin, 5 μg/ml thymidine) following standard procedures.

While the present invention has been described in detail herein, those of ordinary skill in the art will recognize numerous variations and modifications, in what is described, that are within the spirit of the invention. Such variations and modifications are within the scope of the invention as described and claimed herein.

That which is claimed is:

1. An isolated DNA fragment, comprising a sequence of nucleotides that encodes the γ-subunit of a rabbit skeletal muscle calcium channel that has the amino acid sequence set forth in FIG 1.

2. The DNA fragment of claim 1, wherein the β-subunit is encoded by the sequence of nucleotides set forth in FIG. 1.

3. An eukaryotic cell transformed with the DNA fragment of claim 1.

4. An eukaryotic cell transformed with the DNA fragment of claim 2.

5. An isolated DNA fragment, comprising a sequence of nucleotides that encodes the γ-subunit of a DHP-sensitive rabbit skeletal muscle calcium channel.

6. An eukaryotic cell transformed with heterologous DNA, wherein the heterologous DNA comprises the DNA fragment of claim 5.

* * * * *

UNITED STATES PATENT AND TRADEMARK OFFICE

CERTIFICATE OF CORRECTION

PATENT NO. : 5,386,025

DATED : January 31, 1995

INVENTOR(S) : Scott D. Jay, Steven B. Ellis, Michael M. Harpold and Kevin P. Campbell It is certified that error appears in the above-indentified patent and that said Letters Patent is hereby corrected as shown below:

- Column 20, claim 2, line 8, after "the" (second occurrence), delete "$\beta$" and replace with --$\gamma$--.

Signed and Sealed this

Twenty-fifth Day of April, 1995

Attest:

BRUCE LEHMAN

*Attesting Officer* *Commissioner of Patents and Trademarks*

UNITED STATES PATENT AND TRADEMARK OFFICE
CERTIFICATE OF CORRECTION

PATENT NO. : 5,386,025

DATED : January 31, 1995

INVENTOR(S) : JAY, Scott D.; ELLIS, Steven B.; HARPOLD, Michael M.; CAMPBELL, Kevin P.

It is certified that error appears in the above-indentified patent and that said Letters Patent is hereby corrected as shown below:

On the title page: Item [73]

Assignee: after "The Salk Institute Biotechnology/Industrial Associates, San Diego, Calif." add --University of Iowa, Iowa City, Iowa--;

On the title page: Item [56] Other Publications page 2, Sher, et al., after "al.," delete "w" and replace with the Greek letter --ω--;

page 2, Hubbard, et al., after "asparagine-linked," delete "oligosaccharides$^{1,2}$," and replace with --oligosaccharides-- page 3, Biel, et al., after "409-412 (1990)" delete "CHECK";

page 3, Snutch, et al., after "3391-3395 (1990)" delete "CHECK";

page 3, Campbell, et al., after "251-257 (1989)" delete "CHECK";

page 3, Dascal, et al., after "in" delete "Xenopus" and replace with the italicized --*Xenopus*--;

page 3, Jay, et al., after "the" delete "y" and replace with the Greek letter --γ--; and page 3, Carbone, et al., after "170-179 (1990)" delete "(best available copy submitted)".

UNITED STATES PATENT AND TRADEMARK OFFICE

CERTIFICATE OF CORRECTION

PATENT NO. : 5,386,025

DATED : January 31, 1995

INVENTOR(S) : JAY, Scott D.; ELLIS, Steven B.; HARPOLD, Michael M.; CAMPBELL, Kevin P.

It is certified that error appears in the above-indentified patent and that said Letters Patent is hereby corrected as shown below:

column 4, line 40, after "in" delete "Xenopus laevis" and replace with the italicized --*Xenopus laevis*--;

column 4, line 50, after "al.," delete "Trends in Pharmacology. Sci." and replace with the italicized --*Trends in Pharmacolog. Sci.*--;

column 6, lines 16 & 17, delete "Nature" and replace with italicized --Naturecolumn 7, line 49, after "al.," delete "Science" and replace with the italicized --*Science*--;

column 10, line 25, after "Campbell" delete "ibid." and replace with the italicized --*ibid.*--;

column 10, line 26, after "32" delete "KD" and replace with --kD--;

column 11, line 8, after "The" delete "βspecific" and replace with --β-specific--;

column 13, line 21, after "Biolabs," delete "Inc." and replace with --Inc.,- column 13, line 7, after "antisera" delete "Affi-62" and replace with --Affi-β--;

UNITED STATES PATENT AND TRADEMARK OFFICE
CERTIFICATE OF CORRECTION

PATENT NO. : 5,386,025 Page 3 of 3

DATED : January 31, 1995

INVENTOR(S) : Jay, Scott D.; Ellis, Steven B.; Harpold, Michael M.; Campbell, Kevin P.

It is certified that error appears in the above-indentified patent and that said Letters Patent is hereby corrected as shown below:

column 14, line 36, after "al.," delete "Supra" and replace with the italicized —*supra*—;

column 14, line 64, after "218" delete "nts" and replace with —nt—;

column 14, line 64, after "176" delete "nts" and replace with —nt—;

column 15, line 17, after "by" delete "Ruth" and replace with —Ruth,—;

column 15, line 20, after "by" delete "Ruth" and replace with —Ruth,—;

column 15, line 37, after "al.," delete "1985," and replace with —(1985)—;

column 17, line 13, after "are" delete "Ltk-cells" and replace with —$Ltk^-$ cells—;

column 17, line 58, after "plasmid" delete "(pGEM3 +" and replace with —pGEM3 +— column 18, line 43, after "end" delete "of$\beta$" and replace with —of $\beta$—; and column 19, line 7, after "transfecting" delete "Ltk-cells" and replace with —$Ltk^-$ cells—.

Signed and Sealed this

Ninth Day of January, 1996

Attest:

BRUCE LEHMAN

Attesting Officer

*Commissioner of Patents and Trademarks*